(12) United States Patent
Hartshorn et al.

(10) Patent No.: US 7,972,786 B2
(45) Date of Patent: Jul. 5, 2011

(54) DETECTION AND ANALYSIS OF INFLUENZA VIRUS

(75) Inventors: Cristina Hartshorn, Needham, MA (US); Kenneth E. Pierce, Natick, MA (US); Arthur Henry Reis, Jr., Arlington, MA (US); John E. Rice, Quincy, MA (US); J. Aquiles Sanchez, Framingham, MA (US); Lawrence J. Wangh, Auburndale, MA (US)

(73) Assignee: Brandeis University, Waltham, MA (US)

( * ) Notice: Subject to any disclaimer, the term of this patent is extended or adjusted under 35 U.S.C. 154(b) by 515 days.

(21) Appl. No.: 11/822,536

(22) Filed: Jul. 6, 2007

(65) Prior Publication Data

US 2009/0081648 A1 Mar. 26, 2009

Related U.S. Application Data

(60) Provisional application No. 60/819,000, filed on Jul. 7, 2006.

(51) Int. Cl.
*C12Q 1/68* (2006.01)
*C07H 21/04* (2006.01)

(52) U.S. Cl. .................... 435/6; 536/23.1; 536/24.32

(58) Field of Classification Search ............ 536/23.1, 536/24.32; 435/6
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,965,188 A | * | 10/1990 | Mullis et al. ............. 435/6 |
| 5,925,517 A | | 7/1999 | Tyagi et al. |
| 6,037,130 A | | 3/2000 | Tyagi et al. |
| 6,103,476 A | | 8/2000 | Tyagi et al. |
| 6,150,097 A | | 11/2000 | Tyagi et al. |
| 6,461,814 B1 | | 10/2002 | Spinella |
| 7,198,897 B2 | | 4/2007 | Wangh et al. |
| 2004/0023269 A1 | | 2/2004 | Li et al. |
| 2006/0177842 A1 | | 8/2006 | Wangh et al. |
| 2006/0217338 A1 | * | 9/2006 | Lu et al. ................. 514/44 |

OTHER PUBLICATIONS

Lowe et al. Nucleic acid research, vol. 18(7), 1990.*
The attached nucleic acid sequence search reports.*
Romanova et al. Virology, 2003, vol. 307, p. 90-97.*
Emerging Infectious Diseases, 2005, vol. 11(10), p. 1515-1521.*
Tyagi, et al., "Molecular Beacons: Probes that Fluoresce upon Hybridization", *Nature Biotechnology*, vol. 14, pp. 303-308 (Mar. 1996).
Tyagi, et al., "Multicolor molecular beacons for allele discrimination", *Nature Biotechnology*, vol. 16, pp. 49-53 (Jan. 1998).
Kostrikis, et al., "Spectral Genotyping of Human Alleles", *Science*, vol. 279, pp. 1228-1229 (Feb. 1998).
Salk, et al., "Direct amplification of single-stranded DNA for pyrosequencing using linear-after-the-exponential (Late)-PCR", *Analytical Biochemistry*, vol. 353, pp. 124-132 (2006).
Hartshorn, et al., "Rapid, single-tube method for quantitative preparation and analysis of RNA and DNA in samples as small as one cell", *BMC Biotechnology*, vol. 5:2, pp. 1-13, (2005).
Raja, et al., "Temperature-controlled primer Limit for Multiplexing of Rapid Quantitative Reverse Transcription-PCR Assays: Application to Intraoperative Cancer Diagnostics", *Clinical Chemistry*, vol. 48:8, pp. 1329-1337 (2002).
Raja, et al., "Technology for Automated, Rapid, and Quantitative PCR or Reverse Transcription-PCR Clinical Testing", *Clinical Chemistry*, vol. 51:5, pp. 882-890 (2005).
Stanley, et al., "Multiplexed tandem PCR: gene profiling from small amounts of RNA using SYBR Green detection", *Nucleic Acids Research*, vol. 33, No. 20, pp. 1-9 (2005).

* cited by examiner

*Primary Examiner* — Kenneth R. Horlick
*Assistant Examiner* — Joyce Tung
(74) *Attorney, Agent, or Firm* — Casimir Jones, S.C.

(57) ABSTRACT

An assay comprising more than one primer pair and more than one detection probe, a low copy number synthetic amplicon corresponding to each of the primer pairs. The assay can detect and distinguish between various sub-types and strains of an influenza virus using any suitable nucleic acid amplification technique. Related kits and methods are also described.

5 Claims, 31 Drawing Sheets

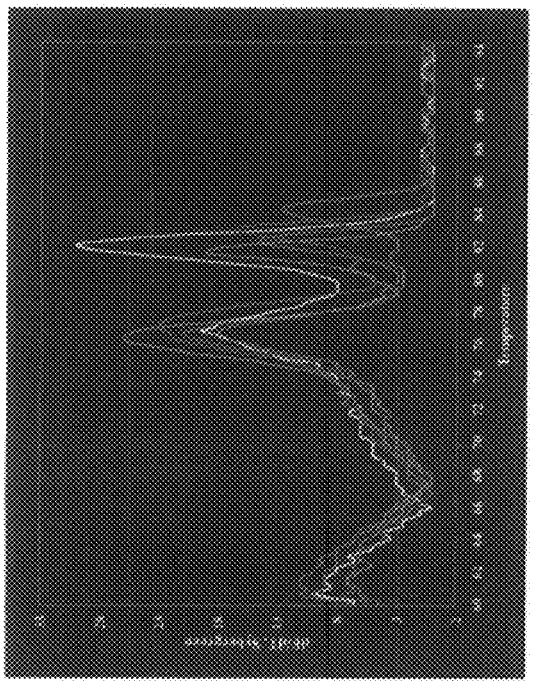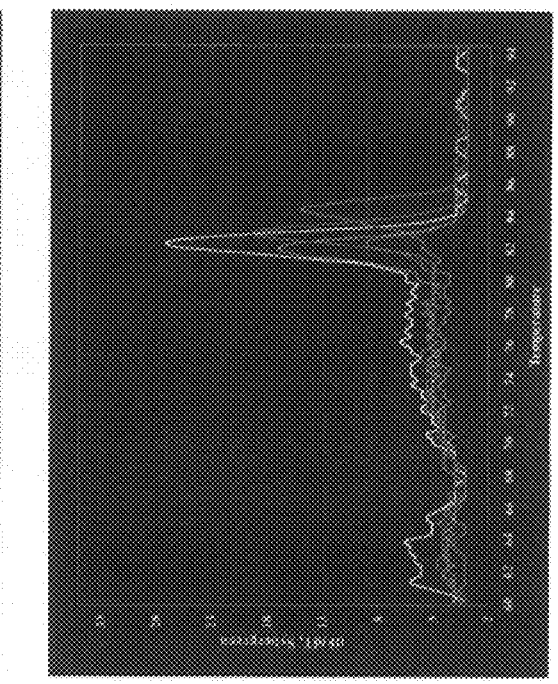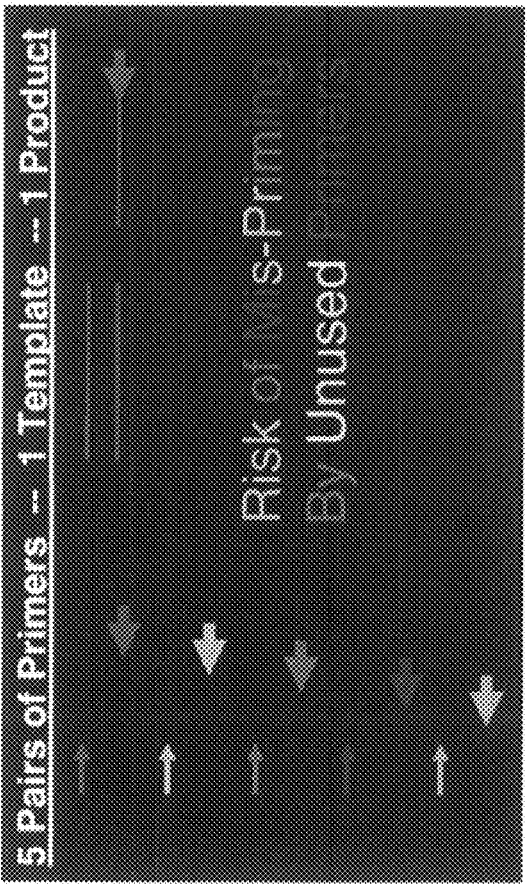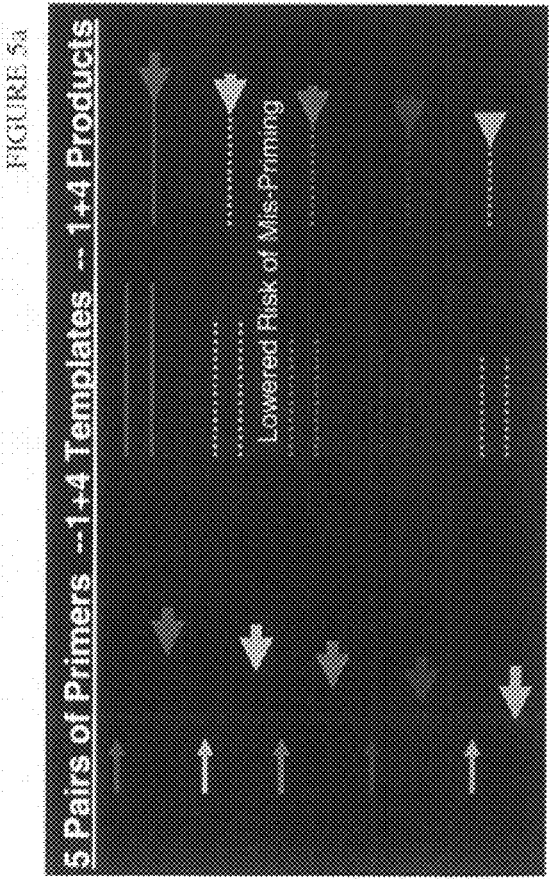
FIGURE 5a  FIGURE 5b

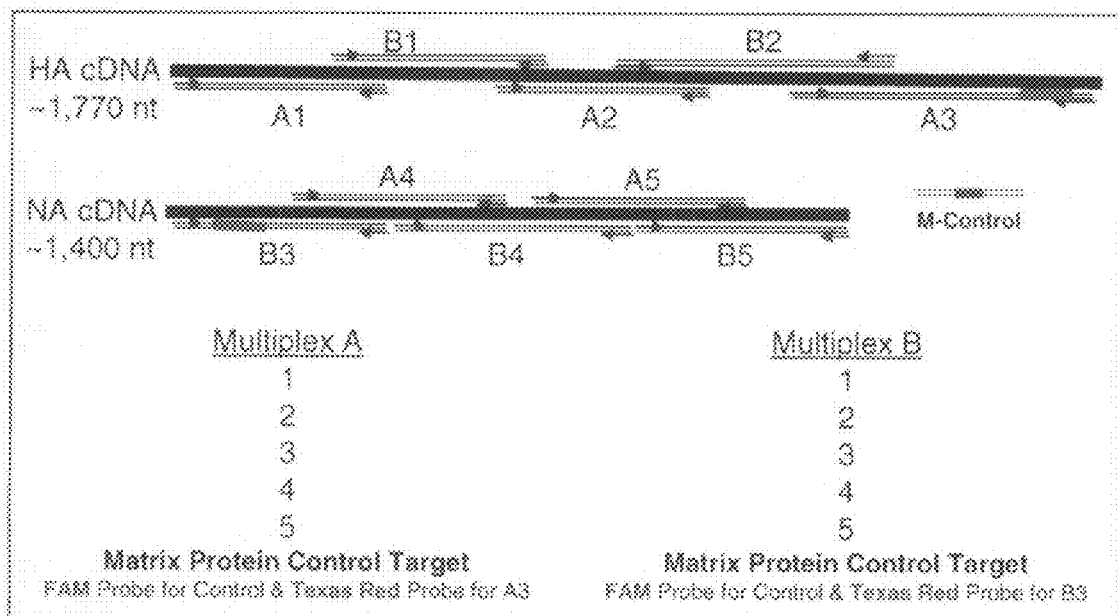
FIGURE 15
FIGURE 17
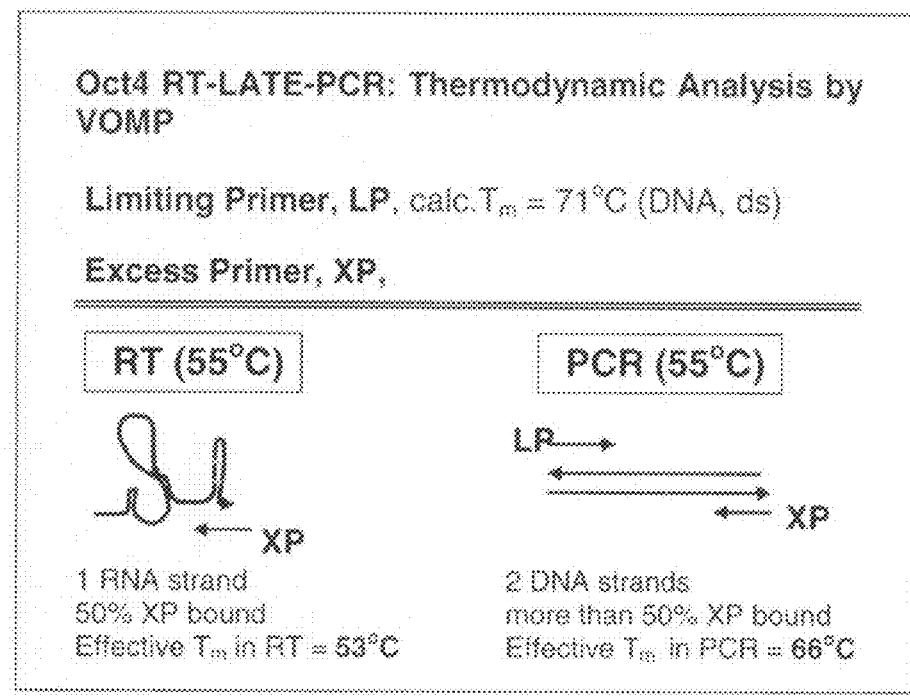

Fig. 12

Clustal comparison of Influenza Virus M RNA Sequences M RNA Segment

```
SeqA  Name    Len(nt)   SeqB  Name    Len(nt)   Score
=======================================================
1     H3N2M   989       2     H1N1M   985       91
1     H3N2M   989       3     H5N1M   1039      86
1     H3N2M   989       4     BM      1076      5
2     H1N1M   985       3     H5N1M   1039      87
2     H1N1M   985       4     BM      1076      5
3     H5N1M   1039      4     BM      1076      4
```

```
H3N2M  ------------TAGATATTGAAAGATGAGCCTTCTAACCGAGGTCGAAACGTATGTTCT  48
H1N1M  -------------------------ATGAGTCTTCTAACCGAGGTCGAAACGTACGTTCT  35
H5N1M  AGCAAAAGCAGGTAGATGTTGAAAGATGAGTCTTCTAACCGAGGTCGAAACGTACGTTCT  60
BM     -------------------------ATGTCGCTGTTTGGAGACACAATTGCCTACCTGCT  35
                                ***    **   *    **        *  **    * **

H3N2M  CTCTATCGTTCCATCAGGCCCCCTCAAAGCCGAAATCGCGCAGAGACTTGAAGATGTCTT  108
H1N1M  CTCTATCGTCCCGTCAGGCCCCCTCAAAGCCGAGATCGCACAGAGACTTGAAAATGTCTT  95
H5N1M  CTCTATCATCCCGTCAGGCCCCCTCAAAGCCGAGATCGCGCAGAAACTTGAAGATGTCTT  120
BM     TTCATTGACAGAAGATGGAGAAGGCAAAGCAGAACTAGCAGAAAAATTACACTGTTGGTT  95
         **    *           **       ****** **   * **    * * * *    *     **

H3N2M  TGCTGGGAAAAACACAGATCTTGAGGCTCTCATGGAATGGCTAAAGACAAGACCAATCCT  168
H1N1M  TGCTGGAAAGAATACCGATCTTGAGGCTCTCATGGAATGGCTAAAGACAAGACCAATCCT  155
H5N1M  TGCAGGAAAGAACACCGATCTCGAGGCTCTCATGGAGTGGCTAAAGACAAGACCAATCCT  180
BM     CGGTGGGAAAGAATTTGACCTAGACTCTGCCCTGGAATGGATAAAAACAAAAGATGCTT   155
         *    ** **    *     ** ** **   **    *  **** ***  ****  *    *    *    * *

H3N2M  GTCACCTCTGACTAAGGGGATT--TTGGGGTTTGTGTTCACGCTCACCGTGCCCAGTGAG  226
H1N1M  GTCACCTCTGACTAAGGGGATT--TTAGGATTTGTGTTCACGCTCACCGTGCCCAGTGAG  213
H5N1M  GTCACCTCTGACTAAAGGGATT--TTGGGATTTGTATTCACGCTCACCGTGCCCAGTGAG  238
BM     AACTGATAT-ACAAAAAGCACTAATTGGTGCCTCTATCTGC-TTTTTAAAACCCAAAGAC  213
         *    *  ** **   * * *    * *  *       *    ****  **

H3N2M  CGAGGACTGCAGCGTAGACGCTTTGTCCAAAATGCCCTCAATGGGAATGGGGATCCAAAT  286
H1N1M  CGAGGACTGCAGCGTAGACGCTTTGTCCAAAATGCCCTTAATGGGAATGGGGATCCAAAT  273
H5N1M  CGAGGACTGCAGCGTAGACGCTTTGTCCAGAATGCCCTAAATGGAAATGGAGATCCAAAT  298
BM     CAGGAAAGAAAAAGAAGATTCAT----CACAGAGCCTCTATCAGGAATGGGAACAACAGC  269
         *  *        *   *  ***  * *       ** * **        *     *  ***** *     *

H3N2M  AACATGGACAAAGCAGTTAAACTGTAT-----AGAAAACTTAAGAGGGAGATAACATTCC  341
H1N1M  AATATGGACAGAGCAGTTAAACTGTAT-----CGAAAGCTTAAGAGGGAGATAACATTCC  328
H5N1M  AATATGGATAGAGCAGTCAAGCTATAT-----AAGAAGCTGAAAAGAGAAATAACATTCC  353
BM     AACA-AAAAGAAAGGCCTGATTCTAGCTGAGAGAAAAATGAGAAGATGTGTGAGCTTTC   328
         **        *    *     *          *   **   *    **        * *    **          *    *    **
```

Fig. 12 (cont.)

```
H3N2M  ATGGGGCCAAAGAAATAGCACTCAGTTATTCTGCTGGTGCACTTGCCAGTTGCATGGGCC  401
H1N1M  ATGGGGCCAAAGAAATAGCACTCAGTTATTCTGCTGGTGCACTTGCCAGTTGTATGGGAC  388
H5N1M  ATGGGGCTAAGGAGGTCGCACTCAGCTACTCAACCGGTGCACTTGCCAGTTGCATGGGTC  413
BM     ATGAAGCATTTGAAATAGCAGAAGGCCATGAAAGCTCAGCGCTACTATACTGTCTCATGG  388
       ***  **    **  * ***       *    *          ** **    **  *

H3N2M  TCATATACAATAGGATGGGGGCTGTAACCACCGAAGTGGCATTTGGCCTGGTATGTGCAA  461
H1N1M  TCATATACAACAGGATGGGGGCTGTGACCACCGAATCAGCATTTGGCCTTATATGCGCAA  448
H5N1M  TCATATACAACAGGATGGGAACGGTGACTACGGAAGTGGCTTTTGGCCTAGTGTGTGCCA  473
BM     TCATGTACCTGAATCCTGGAAATTATTCAATGCAAGTAAAACTAGGAACGCTCTGTGCTT  448
       ****  ***  *    **        *  *  **       *  **      * ** **

H3N2M  CATGTGAACAGATTGCTGACTCCCAGCACAGGTCTCATAGGCAAATGGTGGCAACAACCA  521
H1N1M  CCTGTGAACAGATTGCCGACTCCCAGCATAAGTCTCATAGGCAAATGGTAACAACAACCA  508
H5N1M  CTTGTGAGCAGATTGCAGATTCACAGCATCGGTCTCACAGACAGATGGCAACTACCACCA  533
BM     TGTGCGAGAAACAAGCATCACATTCACACAGGGCTCATAGCAGAGCAGCGAGATCTTCAG  508
         **  **   *  **     ** *    *  ****  **        *      *  *

H3N2M  ATCCATTAATAAAACATGAGAACAGGATGGTTTTGGCCAGCACTACAGCTAAAGCTATGG  581
H1N1M  ACCCATTAATAAGACATGAGAACAGAATGGTTCTGGCCAGCACTACAGCTAAGGCTATGG  568
H5N1M  ACCCACTAATCAGACATGAGAACAGAATGGTGCTGGCCAGCACTACAGCTAAGGCTATGG  593
BM     TGCCTGGAGTGAGACGAGAAATGCAGATGGTCTCAGCTATGAACACAGCAAAAACAATGA  568
         **    *   *   **  **  *   ***** *    *        *  *   ***

H3N2M  AGCAAATGGCTGGATCAAGTGA------GCAGGCAGCGGAGGCCATGGAGATTGCTAGTC  635
H1N1M  AGCAAATGGCTGGATCGAGTGA------ACAAGCAGCTGAGGCCATGGAGGTTGCTAGTC  622
H5N1M  AGCAGATGGCAGGATCAAGTGA------GCAGGCAGCGGAAGCCATGGAGATCGCTAATC  647
BM     ATGGAATGGGAAAAGGAGAAGACGTCCAAAAACTGGCAGAAGAGCTGCAAAGCAACATTG  628
       *    ****   *      **    *    ** **  **   **  *        *  *

H3N2M  AGG--CCAGG--CAAATGGTGCAGGCAATGAGAACC-GTTGGGACTCATCCTAGCTCCAG  690
H1N1M  AGG--CCAGG--CAGATGGTGCAGGCAATGAGAGCC-ATTGGGACTCATCCTAGCTCTAG  677
H5N1M  AGG--CTAGG--CAGATGGTGCAGGCAATGAGGACA-ATTGGGACTCATCCTAACTCTAG  702
BM     GAGTACTGAGATCTCTTGGGGCAAGTCAAAAGAATGGAGAAGGAATTGCAAAGGATGTAA  688
       *    *  *      *   ***  ***  *    **         *** *      *  *

H3N2M  TACTGGTCTAAGAGATGATCTTCTTGAAAATTTGCAGACCTATCAGAAACGAATGGGGGT  750
H1N1M  CACTGGTCTGAAAAATGATCTCCTTGAAAATTTGCAGGCCTATCAGAAACGAATGGGGGT  737
H5N1M  TGCTGGTCTGAGAGATAATCTTCTTGAAAATTTGCAGGCCTACCAGAAACGAATGGGAGT  762
BM     TGGAAGTGCTAAAGCAGAGCTCTATGGGAAATT-CAG--CTCTTGTGAAGAAATATCTAT  745
         **    *  *  *  **   ** **   ***  **     **  *  ***      *

H3N2M  GCAGATGCAACGATTCAAGTGACCTGCTGTTGTTGCTGCGAGTATCATTGGGATCTTGC  810
H1N1M  GCAGATGCAACGATTCAAGTGATCCTCTTGTTGTTGCCGCAAGTATAATTGGGATTGTGC  797
H5N1M  GCAGATGCAGCGATTCAAGTGATCCTATTGTTGTTGCCGCAAATATCATTGGGATCTTGC  822
BM     AATGCTCGAACCATTTCAG--ATTCTTTCAATTTGTTCTTTTATCTTATCAG--CTCTCC  801
        *  *  * **  ***  ***    *       *   * *    *  **       *  *

H3N2M  ACTTGATATTGTGGATTCTTGATCGTCTTTTTTTCA-AATGCATCTATCGACTCTTCAAA  869
H1N1M  ACCTGATATTGTGGATTATTGATCGCCTTTTTTCCA-AAAGCATTTATCGTATCTTTAAA  856
H5N1M  ACTTGATATTGTGGATTCTTGATCGTCTTTTCTTCA-AATGCATTTATCGTCGCCTTAAA  881
```

Fig. 12 (cont.)

```
BM      ATTTCATGGCTTGGACAATAGGGCATTTGAATCAAATAAAAAGAGGAGTAAACATGAAAA 861
         *  *  **   ****    *  *    *       *  **    *        ***

H3N2M   CACG--------GCCTGAAAAGAGGGCCTTCTACGGAAGGAGTACCTGAGTCTATGAGGG 921
H1N1M   CACG--------GTTTAAAAAGAGGGCCTTCTACGGAAGGAGTACCAGAGTCTATGAGGG 908
H5N1M   TACG--------GTTTGAAAAGAGGGCCTGCTACGGCAGGGGTACCTGAGTCTATGAGGG 933
BM      TACGAATAAAAAGTCCAAACAAAGAGACAATAAACAGAGAGGTATC--AATTT-TGAGAC 918
        ***         *     ** *  ** *         *    ** *** *   *  ****

H3N2M   AAGAATATCGAAAGGAACAGCAGAATGCTGTGGATGCTGACGGCAGT-CATTTTGTCAGC 980
H1N1M   AAGAATATCGAGAGGAACAGCAGAATGCTGTGGATGCTGACGATGGT-CATTTTGTCAGC 967
H5N1M   AAGAGTACCGGCAGGAACAGCAGAGTGCTGTGGATGTTGACGATGGT-CATTTTGTCAAC 992
BM      ACAGTTACCAAAAGAAATCCAGGCCAAAG-AAACAATGAAGGAGGTACTCTCTGACAAC 977
          *   **  *    *  ***   ***    *    *    ** *   *  ** ** *

H3N2M   ATAGAGCTG--------------------------------------------------- 989
H1N1M   ATAGAGCTG--GAGTAAAAA---------------------------------------- 985
H5N1M   ATAGAATTG--GAGTAAAAAACTACCTTGTTTCTACTAATACGGAAGAC----------- 1039
BM      ATGGAGGTATTGAGTGACCACATAATAATTGAGGGCTTTCTGCCGAAGAGATAATAAAA 1037
               **  **  *

H3N2M   -----------------------------------------
H1N1M   -----------------------------------------
H5N1M   -----------------------------------------
BM      ATGGGTGAAACAGTTTTGGAGATAGAAGAATTGCATTAA 1076
```

Fig. 13

Clustal comparison of Influenza Virus HA RNA Sequences

HA RNA Segment

```
SeqA  Name    Len(nt)  SeqB  Name    Len(nt)  Score
====================================================
 1    H3N2HA  1718      2    H5N1HA  1736     28
 1    H3N2HA  1718      3    H1N1HA  1692     37
 1    H3N2HA  1718      4    BHA     1038      3
 2    H5N1HA  1736      3    H1N1HA  1692     64
 2    H5N1HA  1736      4    BHA     1038      4
 3    H1N1HA  1692      4    BHA     1038      5
====================================================

H5N1HA  ------------------------TCATCTGTCAAATGGAGAAAATAGTGCTTCTTTTTG  36
H1N1HA  -----------------------------ATGAAA--GCAAAACTACTGGTCCTGTTAT  28
H3N2HA  TATTAACCATGAAGACTATCATTGCTTTGAGCTACATTCTATGTCTGGTTTTCGCTCAAA  60
BHA     ------------------------------------------------------------

H5N1HA  CAATAGTCAGTCTTGTTAAAAGTGATCAGA---TTTGCATTGGTTACCATGCAAACAACT  93
H1N1HA  GTACATTTACAGCTACATATGCAGACACAA---TATGTATAGGCTACCATGCCAACAACT  85
H3N2HA  AACTTCCCGGAAATGACAACAGCACGGCAACGCTGTGCCTTGGGCACCATGCAGT--ACC 118
BHA     ------------------------------------------------------------

H5N1HA  CGACAGA--GCAGGTTGACACAATAATGGAAAAGAACGTTACTGTTACACATGCCCAAGA 151
H1N1HA  CAACCGA--CACTGTTGACACAGTACTTGAGAAGAATGTGACAGTGACACACTCTGTCAA 143
H3N2HA  AAACGGAACGATAGTGAAAACAATCACGAATGACCAAATTGAAGTTACTAATGCTACTGA 178
BHA     ------------------------------------------------------------

H5N1HA  CATACTGGAAAAGACACACAACGGGAAGCTCTGCGATCTAGATGGAGTGAAGCCTCTAAT 211
H1N1HA  CCTACTTGAGGACAGTCACAACGGAAAACTATGTCTACTAAAAGGAATAGCCCCACTACA 203
H3N2HA  GCTGGTTCAGAGTTCCTCAACAGGTGGAATATGCGA--CAGTCCTCATCAGATCCTTGAT 236
BHA     ------------------------------------------------------------

H5N1HA  TTTGAGAGATTGTAGTGTAGCTGGATGG-CTCCTCGGAAACCCAATGTGTGACGAATTCA 270
H1N1HA  ATTGGGTAATTGCAGCGTTGCCGGATGG-ATCTTAGGAAACCCAGAATGCGAATTACTGA 262
H3N2HA  GGAGA-AAACTGCA-CACTAATAGATGCTCTATTGGGAGACCCTCAGTGTGATGGCTTCC 294
BHA     ------------------------------------------------------------

H5N1HA  TCAATGTGCCGGAATGGTCCTACATAGTGGAGAAGGCCAATCCAGTCAATGACCTCTGTT 330
H1N1HA  TTTCCAAGGAATCATGGTCCTACATTGTAGAAACACCAAATCCTGAGAATGGAACATGTT 322
H3N2HA  AAAATAAGAAATG--GGACCTTTTTGTTGAACGCAGCAAAGCCT----ACAGCAACTGTT 348
```

Fig. 13 (cont.)

```
BHA    ----------------------------------------------------------

H5N1HA ACCCAGGGGATTTCAATGACTATGAAGAATTGAAACACCTATTGAGCAGAATAAACCATT 390
H1N1HA ACCCAGGGTATTTCGCCGACTATGAGGAACTGAGGGAGCAATTGAGTTCAGTATCTTCAT 382
H3N2HA ACCCTTATGATGTGCCGGATTATGCCTCCCTTAGGTCACTAGTTGCCTCATCCGGCACAC 408
BHA    ----------------------------------------------------------

H5N1HA TTGAGAAAATTCAGATCATCCCCAAA---AGTTCTTGGTCCAGTCATGAAGCCTCATTAG 447
H1N1HA TTGAGAGATTCGAAATATTCCCCAAAGAAAGCTCATGGCCCAACCAC---ACCGTAACCG 439
H3N2HA TGGAGTTTAACAATGAAAGCTTCAA---------TTGGACTGGAGTC---ACTCAAAATG 456
BHA    ------------------------------------GATCGAATCTGCACTG  16
                                                            *

H5N1HA GGGTGAGCTCAGCATGTCCATACCAGAGAA--AGTCCTCCTTTTTCAGA--AATGTGGTA 503
H1N1HA GAGTATCAGCATCATGCTCCCATAATGGGA--AAAGCAGTTTTTACAGA--AATTTGCTA 495
H3N2HA GAACAAGCTCTGCTTGTAAAAGGAGATCTA--ATAACAGTTTCTTTAGT--AGATTGAAT 512
BHA    GGATAACATCTTCAAACTCACCTCATGTGGTCAAAACAGCTACTCAAGGGGAGGTCAATG  76
          *    *  *            *    * *  *  * **   *

H5N1HA TGGCTTATCAAAAAGAACAGTACATACCCAACAATAAAGAGGAGCTACAATAATACCAAC 563
H1N1HA TGGCTGACGGGGAAGAATGGTTTGTACCCAAACCTGAGCAAGTCCTATGTAAACAACAAA 555
H3N2HA TGGTTGACCCACTTAAAATTCAAATACCCAGCATTGAACGTGACTATGCCAAACAATGAA 572
BHA    TGACTGGTGTGATACCACTGACAACAAC-ACCAACAAAATCTTATTTTGCAAATCTCAAA 135
       ** *           *         * * *            *         **    *

H5N1HA CAAGAAGATCTTTTGGTACTGTGGGGGATTCACCATCCTAATGATGCGGCAGAGCAGACA 623
H1N1HA GAGAAAGAAGTCCTTGTACTATGGGGTGTTCATCACCCGCCTAACATAGGGGACCAAAGG 615
H3N2HA AAATTTGACAAATTGTACATTTGGGGGGTTCACCACCCGGGTACGGACAATGACCAAATT 632
BHA    GGAACAAGGACCAGAGGGAAACTATGCCCAGACTGTCTCAACTGTACAGATCTGGATGTG 195
                                      *    *    *                 *

H5N1HA AAGCTCTATCAAAACCCAACCACCTATATT---TCCGTTGGGACATCAACACTAAACCAG 680
H1N1HA GCCCTCTATCATACAGAAAATGCTTATGTC---TCTGTAGTGTCTTCA-CATTATAGCAG 671
H3N2HA AGCCTATAT---GCTCAAGCTTCAGGAAGA---ATCACAGTCTCTACCAAAAGAAGCCAA 686
BHA    GCCTTGGGCAGGCCAATGTGTGTGGGACCACACCTTCTGCGAAAGCTTCAATACTCCAC 255
          *                                  *   *   *  *   **

H5N1HA A-GATTG--GTACCAAGAATAGCTACTAGATCCAAAGTAAACGGGCAAAGTGGAAGGATG 737
H1N1HA AAGATTC--ACCCCAGAAATAGCCAAAAGACCCAAAGTAAGAGATCAGGAAGGAAGAATC 729
H3N2HA CAAACTGTAATCCCGAATATCGGATCTAGACCCAGGGTAAGGGATATCCCCAGCAGAATA 746
BHA    GAAGTCA---GACCTGTTACATCCGGGTGCTTTCCTATAATGCACGACAGAACAAAAATC 312
                **    *         *      ***              *   **

H5N1HA GAGTTCTTCTGGACAATTTTAAAACCGAATGATGCAATCAACTTCGA--GAGTAATGGAA 795
H1N1HA AACTACTACTGGACTCTGCTGGAACCTGGGGATACAATAATATTTGA--GGCAAATGGAA 787
H3N2HA AGCATCTATTGGACAATAGTAAAACCGGGAGACATACTTTTGATTAA--CAGCACAGGGA 804
BHA    AG--GCAACTAGCCAATCTTC---TCAGAGGATATGAAAATATCAGGTTATCAACCCAAA 367
       *   *  *  *    *       *    **            *   *         *
```

Fig. 13 (cont.)

```
H5N1HA  ATTTCATTGCTCCAGAATATGCATACAAAATTGTCAAGAAAGGGGACTCAACAATTATGA  855
H1N1HA  ATCTAATAGCGCCATGGTATGCTTTTGCACTGAGTAGAGGCTTTGGATCAGGAATCATCA  847
H3N2HA  ATCTAATTGCTCCTCGGGGTTACTTCAAAATACGAAGTGGGAAAAGCTCAATAA---TGA  861
BHA     ACGTTATCGATGCAGAAAAGGCACCAGGAGGACCCTACAGACTTGGAACCTCAGGATCTT  427
        *  * ** *     *                  *                  *   *

H5N1HA  AAAGTGAATTGGAATATGGTAACTGCAACACCAAGTGTCAAACTCCAATGGGGGCGATAA  915
H1N1HA  CCTCAAATGCACCAATGGATGAATGTGATGCGAAGTGTCAAACACCTCAGGGAGCTATAA  907
H3N2HA  GATCAGATGCACCCATTGGCAAATGCAATTCTGAATGCATCACTCCAAATGGAAGCATTC  921
BHA     GCCCTAACGC---TACCAGTAAAAGCGGATTT---TTCGCAACAATGGCTTGGGCTGTCC  481
            *         * *           *   *  **     *     *     *

H5N1HA  ACTCTAGTATGCCATTCCACAATATACACCCTCTCACCATCGGGGAATGCCCCAAATATG  975
H1N1HA  ACAGCAGTCTTCCTTTCCAGAATGTACACCCAGTCACAATAGGAGAGTGTCCAAAGTATG  967
H3N2HA  CCAATGACAAACCATTTCAAAATGTAAACAGGATCACATATGGGGCCTGTCCCAGATATG  981
BHA     CAAAGGACAACAACAAAAATGCAACGAACCCACTAACAGTAGAAG--TACCATACATTTG  539
              *            **   * **      *   *    *   *  *  *  **

H5N1HA  T-GAAATCAAACAGATTAGTCCTTGCGACTGGGCTCAGAAATAGCCCTCAAAGAGAGAGA  1034
H1N1HA  T-CAGGAGTGCAAAATTAAGGATGGTTACAGGACTAAGGAACATCCC------------A  1014
H3N2HA  T-TAAGCAAAACACTCTGAAATTGGCAACAGGGATGCGAAATGTACC------------A  1028
BHA     TACAGAAGGGGAAGACCAAATTACTGTTTGGGGGTTCCATTCAGATA-----------AC  588
        * *    *                     **  *

H5N1HA  AGAAGAAAAAAGAGAGGATTATTTGGAGCTATAGCAGGTTTTATAGAGGGAGGATGGCAG  1094
H1N1HA  TCCATTCAATCCAGAGGTTTGTTTGGAGCCATTGCCGGTTTCATTGAAGGGGGTGGACT  1074
H3N2HA  GAGAAACAAACTAGAGGCATATTTGGCGCAATCGCGGGTTTCATAGAAAATGGTTGGGAG  1088
BHA     AAAACCCAAATGAAGAACCTCTATGGAG-----ACTCAAATCCTCAAAAGTTCACCTCAT  643
           *   **   *       *  * ***  *      *       *    *

H5N1HA  GGAATGGTAGATGGTTGGTATGGGTACCACCATAGCAATGAGCAGGGGAGTGGGTACGCT  1154
H1N1HA  GGAATGGTAGATGGGTGGTATGGTTATCATCATCAGAATGAGCAAGGATCTGGCTATGCT  1134
H3N2HA  GGAATGGTGGATGGTTGGTACGGTTTCAGGCATCAAAATTCTGAGGGAATAGGACAAGCA  1148
BHA     CTGCTAATGGAGTAACCACACA-TTATGTTTCTCAGATTGGCGGCTTCCCAGATCAAACA  702
              *  **        *    *       *  * *                *  * *

H5N1HA  GCAGACAAAGAATCCACTCAAAAGGCAATAGATGGAGTCACCAATAAGGTCAACTCGATC  1214
H1N1HA  GCAGATCAAAAAAGTACACAAAATGCCATTAACGGGATTACAAACAAGGTGAATTCTGTA  1194
H3N2HA  GCAGATCTCAAAAGCACTCAAGCAGCAATCAACCAAATCAATGGGAAGCTGAATAGGTTG  1208
BHA     GAAGACGGAGGACTACCACAAAGCGGCAGAATTGTCGTTGATTACATGATGCA---AAAA  759
          * ***       *   * ***   *     *              *  ****

H5N1HA  ATTGACAAAATGAACACTCAGTTTGAGGCCGTTGGAAGGGAATTTAACAACTTAGAAAGG  1274
H1N1HA  ATTGAGAAAATGAACACTCAATTCACAGCTGTGGGCAAAGAATTCAACAAATTGGAAAGA  1254
H3N2HA  ATCGGGAAACCAACGAGAAATTCCATCAGATTGAAAAGAATTCTCAGAAGTAGAAGG  1268
BHA     CCTGGGAAAACAGGAAC--AATT---GTCTATCAAAGAGGTGTTTTGTTGCCTCAAAAGG  814
           *   ****     *     * **         *    *   **   *   ** *

H5N1HA  AG-AATAGAGAATTTAAACAAGAAGATGGAAGACGGGTTCCTAGATGTCTGGACTTATAA  1333
H1N1HA  AG-GATGGAAAACTTAAATAAAAAAGTTGATGATGGGTTTCTAGACATTTGGACATATAA  1313
H3N2HA  AG-AATTCAGGACCTCGAGAAATATGTTGAGGACACTAAAATAGATCTCTGGTCATACAA  1327
BHA     TGTGGTGCGCGAGTGGCAGGAGCAAAGTAATAAAAGGGTCCTTGCCTTT--AATTGGTGA  872
```

Fig. 13 (cont.)

```
              *    *        *    *   *       *   *          * *   *              *
H5N1HA  TGCTGAACTTCTGGTTCTCATGGAAAATGAGAGAACTCTAGACTTTCATGACTCAAATGT  1393
H1N1HA  TGCAGAATTGTTGGTTCTACTGGAAAATGAAAGGACTTTGGATTTCCATGACTCCAATGT  1373
H3N2HA  CGCGGAGCTTCTTGTTGCCCTGGAGAACCAACATACAATTGATCTAACTGACTCAGAAAT  1387
BHA     AGCAGA-----TTGCCTTCATGAAAAAT------ACGGTGGATTAAACAAAAGCAAGCCT   921
              ** **        * *       ** * **         **  * **        *      *     *

H5N1HA  CAAGAACCTTTACGACAAGGTCCGACTACAGCTTAGGGATAATGCAAAGGAACTGGGTAA  1453
H1N1HA  GAAGAATCTGTATGAGAAAGTAAAAAGCCAATTAAAGAATAATGCCAAAGAAATAGGAAA  1433
H3N2HA  GAACAAACTGTTTGAAAGAACAAAGAAGCAACTGAGGGAAAATGCTGAGGATATGGGCAA  1447
BHA     TA-----CTACACAGGAGAACATGCAAA-AGCCATAGGAAATTGCCCA--ATATGGGTGA   973
            *    **     *          *            * * * ***  *   *    *  **  *

H5N1HA  CGGTTGTTTCGAGTTCTATCA-TAAATGTGATAATGAATGTATGGAAAGTGTAAGAAACG  1512
H1N1HA  CGGGTGTTTTGAATTCTATCA-CAAGTGTAACAATGAATGCATGGAGAGTGTGAAAAATG  1492
H3N2HA  TGGTTGTTTCAAAATATACCA-CAAATGTGACAATGCCTGCATAGGGTCAATCAGAAATG  1506
BHA     AAACACCTTTGAAGCTTGCCAATGGAACCAAATATAGACCTCCTGCAAAACTATTAAAGG  1033
              **   *    *     *  **       *   **           *       *   *  *** *

H5N1HA  GAACGTATGACTACCCGCAGTATTCAGAAGAAGCAAGACTAAAAAGAGAGGAAATAAGTG  1572
H1N1HA  GAACTTATGACTATCCAAAATATTCCGAAGAATCAAAGTTAAACAGGGAGAAAATTGATG  1552
H3N2HA  GAACTTATGACCATGATGTATACAGAGATGAAGCATTAAACAACCGGTTCCAGATCAAAG  1566
BHA     AAAGG-------------------------------------------------------  1038
            * *

H5N1HA  GAGTAAAATTGGAATCAATAGGAATTTACCAAATACTGTCAATTTATTCTACAGTGGCGA  1632
H1N1HA  GAGTGAAATTGGAATCAATGGGAGTCTATCAGATTCTGGCGATCTACTCAACTGTCGCCA  1612
H3N2HA  GTGTTGAGCTGAAGTCAGGATACAAAGATTGGATCCTATGGATTTCCTTTGCCATATCAT  1626
BHA     ------------------------------------------------------------

H5N1HA  GTTCCCTAGCACTGGCAATCATGGTAGCTGGTCTATCCTTATGGATGTGCTCCAATGGGT  1692
H1N1HA  GTTCCCTGGTTCTTTTGGTCTCCCTGGGGGCAATCAGCTTCTGGATGTGTTCCAATGGGT  1672
H3N2HA  GTTTTTTGCTTTGTGTTGTTTTGTTGGGG---TTCATCATGTGGGCCTGCCAAAAAGGCA  1683
BHA     ------------------------------------------------------------

H5N1HA  CGTTACAATGCAGAATTTGCATTTAAATTTGTGAGTTCAGATTG  1736
H1N1HA  CTTTGCAGTGCAGAATATGC------------------------  1692
H3N2HA  ACATTAGGTGCAACATTTGCATTTGAGTGCATTAA---------  1718
BHA     --------------------------------------------
```

Fig. 14

Clustal comparison of Influenza Virus NA RNA Sequences

NA RNA Segment

```
SeqA Name    Len(nt)  SeqB Name    Len(nt)  Score
=================================================
 1   H1N1NA   1409     2   H5N1NA   1392     75
 1   H1N1NA   1409     3   H3N2NA   1410     42
 1   H1N1NA   1409     4   BNA      1463     16
 2   H5N1NA   1392     3   H3N2NA   1410     33
 2   H5N1NA   1392     4   BNA      1463      7
 3   H3N2NA   1410     4   BNA      1463     18
```

```
H1N1NA  -----------------------------------ATGAATCCAAATCAAAAAATAATAA  25
H5N1NA  TTATTGGTCTCAGGGAGCAAAAGCAGGAGTTCAAAATGAATCCAAATAAGAAGATAATAA  60
H3N2NA  -----------------------------------ATGAATCCAAATCAAAAGATAATAA  25
BNA     ---------------------------------------------CCAAAATGAACAA   13
                                                     **   ** **

H1N1NA  CCATTGGATCAATCAGTATAGCAATCGGAATAATTAGTCTAATGTTGCAAATAGGAAATA  85
H5N1NA  CCATCGGATCAATCTGTATGGTAACTGGAATGGTTAGCTTAATGTTACAAATTGGGAACT  120
H3N2NA  CGATTGGCTCTGTTTCTCTCACCATTTCCACAATATGCTTCTTCATGCAAATTGCCATCT  85
BNA     T-GCTACCTTCAACTATACAAACGTTAACCCTATTTCTCACATCAGGGGGAGTATTATTA  72
          *         *               *      *       *      *      *

H1N1NA  TTATTTCAA-TATGGGCTAGTCACTCAATCCAAACTGGAAGTCAAAACCACACTGGAGTA  144
H5N1NA  TGATCTCAA-TATGGGTCAGTCATTCAATTCACACAGGGAATCAACACAAAGCTG-----  174
H3N2NA  TGATAACTACTGTAACATTGCATTTCAAGCAATAT--GAATTCAACTCCCCCCCAAA---  140
BNA     TCACTATATGTGTCAGCTTCATTGTCATACT-TACTATATTCGGATATATTGCTAAAAT-  130
         * *      * *      ***     *       *         *

H1N1NA  TGCAACCAAAGAATCATCACATATGAAAAC-AGCACCTGGGTGAA-TCACACATATGTTA  202
H5N1NA  ---AACCAA---------------------------------------------------  180
H3N2NA  --CAACCAAG---TGATGCTGTGTGAACCA-ACAATAATAGAAAG-AAACATAACAGAGA  193
BNA     TCCCATCAACAGAAATTACTGCACCAACAATGCCATTGGATTGTGCAAACGCATCAAATG  190
           * ***

H1N1NA  ATATTAACAACACTAATGTTGTTGCTGGAAAGGACAAA------ACTTCAG--TGACATT  254
H5N1NA  ---TCAGCAATACTAATTTTCTTACTGAGAAAGCTGTG------GCTTCAG--TAAAATT  229
H3N2NA  TAGTGTATCTGACCAACACCACCATAGAGAAGGAAATAT-----GCCCCAAACTAGCAGA  248
BNA     TTCAGGCTGTGAACCGTTCTGCAACAAAAGGGGTGACACTTCTTCTCCCAGAACCGGAGT  250
                      *                     *             **    *

H1N1NA  GGCCGGCAATTCATCT-------CTTTGTTCTATCAGTGGATGGGCTATATACACAAAAG  307
```

Fig. 14 (cont.)

```
H5N1NA  AGCGGGCAATTCATCT-------CTTTGCCCCATTAATGGATGGGCTGTATACAGTAAGG  282
H3N2NA  ATACAGAAATTGGTCAAAGCCG-CAATGTAACATTACAGGATTTGCACCTTTTTCTAAGG  307
BNA     GGACATACCCGCGTTTATCTTGCCCGGGCTCAACCTTTCAGAAAGCACTCCTAATTAGCC  310
                        *           *   *   *            **         *

H1N1NA  ACAACAGCATAAGAATTGGCTCCAAAGG---AGATGTTTTTGTCATAAGAGAACCTTTCA  364
H5N1NA  ACAACAGTATAAGGATCGGTTCCAAGGG---GGATGTGTTTGTTATAAGAGAGCCATTCA  339
H3N2NA  ACAATTCGATTAGGCTTTTCCGCTGGTGG---GGACATCTGGGTGACAAGAGAACCTTATG 364
BNA     CTCATAGATTCGGAGAAACCAAAGGAAACTCAGCTCCCTTGATAATAAGGGAACCTTTTA  370
             *    *   *                    *      *     * * *** ** ** *

H1N1NA  TATCATGTTCTCACTTGGAATGCAGAACCTTTTTTCTGACCCAAGGTGCTCTATTAAATG  424
H5N1NA  TCTCATGCTCCCACTTGGAATGCAGAACTTTCTTTTTGACTCAGGGAGCCTTGCTGAATG  399
H3N2NA  TGTCATGCGATCCTGACAAGTGTTATCAATTTGCCCTTGGGCAGGGAACAACACTAAACA  424
BNA     TTGCTTGTGGACCAAAGGAATGCAAACACTTTGCTCTAACCCACTATGCAGCCCAACCAG  430
          *    * **       *     * **       **       *    **     *

H1N1NA  ACAAACATTCAAATGGGACCGTTAAGGACAGAAGTCCTTATAGGGCCTTAATGAGCTGTC  484
H5N1NA  ACAAGCACTCCAATGGGACTGTCAAAGACAGAAGCCCTCACAGAACATTAATGAGTTGTC  459
H3N2NA  ACGTGCATTCAAATGACACAGTACATGATAGGACCCCTTATCGGACCCTATTGATGAATG  484
BNA     GGGGATACTACAATGGAACAAGAGGAGACAGAAACAAGCTGAGGCATCTAATTTCAGTCA  490
          *  *   **** **       **  **   *           *      ** *

H1N1NA  CTCTAGGTGAAGCTCCGTCCCCATACAATTCAAAGTTTGAATCAGTTGCATGGTCAGCAA  544
H5N1NA  CTGTGGGTGAGGCTCCCTCCCCATATAACTCAAGGTTTGAGTCTGTTGCTTGGTCAGCAA  519
H3N2NA  AGTTAGGT---GTTCCATTTCATCTGGGGACCAAGCAAGTGTGCATAGCATGGTCCAGCT  541
BNA     AATTGGGCAAAATCCCAACAGTAGAAAACTCCATTTTCCACATGGCAGCATGGAGCGGGT  550
          *  **        **                *     *            ** ***

H1N1NA  GCGCATGCCATGATGGCATGGGCTGGTTAACAATCGGAATTTCTGGTCCAGACAATGGAG  604
H5N1NA  GTGCTTGCCATGATGGCACCAGTTGGTTGACAATTGGAATTTCTGGCCCAGACAATGGGG  579
H3N2NA  CAAGTTGTCACGATGGAAAAGCATGGCTGCATGTTTGTGTAACGGGGGATGATAAAAATG  601
BNA     CCGCATGCCATGATGGTAAGGAATGGACATATATCGGAGTTGATGGCCCTGACAATAATG  610
          ** ** ***** *           ***          *   *    **     ** **   *

H1N1NA  CTGTGGCTGTACTAAAATACAACGGCATAATAACTGAAACCATAAAAAGTTGGAAAAAGC  664
H5N1NA  CTGTGGCTGTATTGAAATACAATGGCATAATAACAGACACTATCAAGAGTTGGAGGAATA  639
H3N2NA  CAACTGCTAGCTTCATTTACAATGGGAGGCTTGTAGATAGTATTGTTTCATGGTCCAAAG  661
BNA     CATTGCTCAAAATAAAATATGGAGAAGCATATACTGACACATACCATTCCTATGCAAACA  670
         *          *       **    *          ** *          *     **

H1N1NA  GAATATTAAGAACACAAGAGTCTGAATGTGTCTGTGTGAACGGGTCATGTTTCACCATAA  724
H5N1NA  ACATACTGAGAACTCAAGAGTCTGAATGTGCATGTGTAAATGGCTCTTGCTTTACTGTAA  699
H3N2NA  AAATCCTCAGGACCCAGGAGTCAGAATGCGTTTGTATCAATGGAACTTGTACAGTAGTAA  721
BNA     ACATCCTAAGAACACAAGAAAGTGCCTGCAATTGCATCGGGGGAAATTGTTATCTTATGA  730
          **   * **  *  ** **      **    **  *    ** **       * *
```

Fig. 14 (cont.)

```
H1N1NA    TGACCGATGGCCCGAGTAATGGGGCCGCCTCGTACAAAATCTTCAAGATCGAAAAGGGGA  784
H5N1NA    TGACTGACGGACCAAGTAATGGTCAGGCATCACATAAGATCTTCAAAATGGAAAAAGGGA  759
H3N2NA    TGACTGATGGGAGTGCTTCAGGAAAAGCTGATACTAAAATACTATTCATTGAGGAGGGA   781
BNA       TAACTGATGGCTCAGCTTCAGGTGTTAGTGAATGCAGATTTCTTAAGATTCGAGAGGGCC  790
           * ** ** **     *   **            *    *   *    **      * **

H1N1NA    AGGTTACTAAATCAATAGAGTTGAATGCACCCAATTTTCATTATGAGGAATGTTCCTGT-  843
H5N1NA    AAGTGGTTAAATCAGTCGAATTGGATGCTCCCAATTATCACTATGAGGAATGCTCCTGT-  818
H3N2NA    AAATCGTTCATACTAGCACATTGTCAGGAAGTGCTCAGCATGTCGAGGAGTGCTCCTGC-  840
BNA       GAATAATAAAAGAAATATTTCCAACAGGAAGAATAAAACATACTGAAGAATGCACATGCG  850
           *     *           *           *    **    ** ** **   *  **

H1N1NA    --TACCCAGACACTGGCACAGTGATGTGTGTATGCAGGGACAACTGGCATGGTTCAAATC  901
H5N1NA    --TATCCTGATGCCGGCGAAATCACATGTGTGTGCAGGGATAATTGGCATGGCTCAAATC  876
H3N2NA    --TATCCTCGATATCTTGGTGTCAGATGTGTCTGCAGAGACAACTGGAAAGGCTCCAATA  898
BNA       GATTTGCTAGCAATAAAACCATAGAATGTGCCTGTAGAGATAACAGTTACACAGCAAAAA  910
            *  *         *     ****  ** ** ** **   *  *        * **

H1N1NA    GACCTTGGGTGTCTTTTAA--TCAAAACCTGGATTATCAAATA-GGATACATCTGCAGTG  958
H5N1NA    GGCCATGGGTATCTTTCAA--TCAAAATTTGGAGTATCAAATA-GGATATATATGCAGTG  933
H3N2NA    GGCCCATAGTAGATATAAACATAAAGGATTATAGCATTGTTTCCAGTTATGTGTGCTCAG  958
BNA       GACCCTTTGTCAAATTAAACGTGGAGACTGATACAGCAGAAATAAGATTGATGTGCACAG  970
           * **   **     * **   *      *           * *   * ***    *

H1N1NA    GGGTGTTCGGTGACAATCCGCGTCCCAAAGATGGA---GAGGGCAGCTGTAATCCAGTGA  1015
H5N1NA    GAGTTTTTGGAGACAATCCACGCCCCAATGATGGA---ACAGGTAGTTGTGGTCCGGTGT  990
H3N2HA    GACTTGTTGGAGACACACCCAGAAAAAACGACAGCTCCAGCAGTAGCCATTGCTTGGATC  1018
BNA       AGACTTATTTGGACACCCCCAGACCAGATGATGGAAGCATAACAGGGCCTTGTGAATCTA  1030
              *  ****  **   *        * **   *              *   *

H1N1NA    CTGTTGATGGAGCAG--------ACGGAGTAAAGGGGTTTTCATACAAATATGGTAATGG  1067
H5N1NA    CCTCTAACGGGGCAT--------ATGGGGTAAAGGGTTTTCATTTAAATACGGCAATGG  1042
H3N2NA    CTAACAATGAAGAAGGTGGT--CATGGAGTGAAAGGCTGGGCCTTTGATGATGGAAATGA  1076
BNA       ATGGGGACAAAGGGAGTGGAGGCATCAAGGGAGGATTTGTCCATCAAAGAATGGCATCCA  1090
            *    *             *      *  *  *  *  *    *   *  ** *

H1N1NA    TGTTTGGATAGGAAGGACTAAAAGTAACAGACTTAGAAAGGGGTTTGAGATGATTTGGGA  1127
H5N1NA    TGTCTGGATCGGGAGAACAAAAAGCACTAATTCCAGGAGCGGCTTTGAAATGATTTGGGA  1102
H3N2NA    CGTGTGGATGGGAAGAACGATCAGCGAGAAGTTACGCTCAGGATATGAAACCTTCAAAGT  1136
BNA       AGATTGGAAGGTGGTACTCTCGAACGATGTCTAAAACTAAAAGGATGGGGATGGGCTGT   1150
           *  ****  *           *             *            **         *

H1N1NA    TCCTAATGGATGGACAGATACCGACAGTGATTTCTCAGTGAA---ACAGGATGTTGTGGC  1184
H5N1NA    TCCAAATGGGTGGACTGAAACGGACAGTAGCTTTTCAGTGAA---ACAAGATATCGTAGC  1159
H3N2NA    CATTGAAGGCTGGTCCAACCCTAATTCCAAATTGCAGATAAATAGGCAAGTCATAGTTGA  1196
BNA       ATGTCAAGTATGATGGAGACCCA----TGGGCTGACAGTGAT-GCCCTTGCTTTTAGTGG  1205
            *  **          *           *    *  *      *    *    *

H1N1NA    AATAACTGATTGGTCAGGGTACAGCGGAAGTTTCGTTCAACATCCTGAGTTAACAGGATT  1244
H5N1NA    AATAACTGATTGGTCAGGATATAGCGGGAGTTTTGTCCAGCATCCAGAACTGACAGGACT  1219
H3N2NA    CAGAGGTAATAGGTCCGGTTATTCTGGTATTTTCTCT----------GTTGA-AGGCAA   1244
BNA       AGTAATGGTTTCAATGGAAGAACCTGGTTGGTACTCCTTTGGCTTCGAAATAAAGACAA   1265
```

Fig. 14 (cont.)

```
              *     *     *    *    **   *                    *  *  **
H1N1NA  GGACTGTATAAGACCTTGCTTCTGGGTTGAGTTAGTCAGAGGACTGCCTAGAGAAAATAC  1304
H5N1NA  AGATTGCATAAGACCTTGTTTCTGGGTTGAGTTGATCAGAGGGCGGCCCAAAGAGAGCAC  1279
H3N2NA  AAGCTGCATCAATCGGTGCTTTTATGTGGAGTTGATAAGGGGAAGAAAAGAGGAAACTGA  1304
BNA     GAAATGTGATGTCCCCTGTATTGGGATAGAGATGGT-ACATGATGGTGGAAAAGAGACTT  1324
            **       *   **  *     *  *** *    *  *       *

H1N1NA  AACAATCTGGACTAGTGGGAGCAGCATTTCTTTTTGTGGCGTAAATAGTGATACTGCAAA  1364
H5N1NA  AA---TTTGGACTAGTGGGAGCAGCATATCTTTTTGTGGTGTAAATAGTGACACTGTGGG  1336
H3N2NA  AGTCTTGTGGACCTCAAACAGTATTGTTGTGTTTTGTGGCACCTCAGGTACATATGGAAC  1364
BNA     GGCACTCAGCAGCTACAGCCAT-TTACTGTTTAATGGGCTCAGGACAGCTGCTGTGGGAC  1383
            *   *  *                      *   **  *          *        **

H1N1NA  CTGGTCTTGGCCAGACGGTGCTGAGTTGCCATTCACCATTG-ACAA--------------  1409
H5N1NA  TTGGTCTTGGCCAGACGGTGCTGAATTGCCATTCACCATTG-ACAAGTAGTTGTTCA---  1392
H3N2NA  AGGCTCATGGCCTGATGGGGCGGACATCAATCTCATGCCTATATAA--------------  1410
BNA     ACTGTCACAGGT-GTTAATATGGCTCTGTAATGGAGGAATGGTTGAGTCTGTTCTAAACC  1442
            **   *    *       *     *    *         *    *   *

H1N1NA  --------------------
H5N1NA  --------------------
H3N2NA  --------------------
BNA     CTTTGTTCCTATTTTGTTTGA  1463
```

Fig. 16a

One Temperature End-Point Reading

Four colors with single color probes, some colors used twice
All probes read at 45C except as noted below
for internal controls which are read at 25C

| I. | 1 | ic @ 25C | ic @ 25C | ic @ 25C | ic @ 25C | Most | Sign. @ 40C |
|---|---|---|---|---|---|---|---|
| II | 1 | Matrix | ic @ 25C | ic @ 25C | ic @ 25C | Unlikely | ●○○○ |
| III | 1 2 | Matrix | H5 (no N1) | ic @ 25C | ic @ 25C | | ●●○○ |
| IV | 1 3 | Matrix | ic @ 25C | H1 (no N1) | ic @ 25C | | ●○●○ |
| V | 1 4 | Matrix | ic @ 25C | ic @ 25C | H3 (no N1) | | ●○○● |
| VI | 1 55 | ic @ 25C | ic @ 25C | B virus | B virus | B virus | ●○●● |
| VII | 1 2/6 | Matrix | H5+N1 (H5/1 subtype) | ic @ 25C | ic @ 25C | H5N1 | ●●○○ |
| VIII | 1 3/6 | Matrix | N1 (H5/1 subtype) | H1 | ic @ 25C | H1N1 | ●●●○ |
| IX | 1 6/4 | Matrix | N1 (H5 subtype) | ic @ 25C | H3 | Unlikely | ●●○● |
| X | 1 6 | Matrix | N1 (no HA) | ic @ 25C | ic @ 25C | | ●●○○ |
| XI | 1 4/7 | Matrix | ic @ 25C | N2 (H3 subtype) | H3 | H3N2 | ●○●● |
| XII | 1 7 | Matrix | ic @ 25C | H1+N2 (H3) | ic @ 25C | Unlikely | ●●●○ |
| XIII | 1 7 | Matrix | ic @ 25C | N2 (no HA) | ic @ 25C | | ●●●○ |

FIGURE 16b

| Condition | Probe Result | | Assay Result |
|---|---|---|---|
| No Virus of Type A or Type B<br>Internal Control indicates amplification has occurred. | | 40°C<br>25°C | No virus |
| Type B HA or Type B NA detected, not both<br>Plus Internal Control | | 40°C<br>25°C | Type B virus<br>HA or NA |
| Type B HA and Type B NA detected<br>Plus Internal Control fully saturated | | 40°C<br>25°C | Type B virus<br>HA and NA |
| Type A H5N1 (of H5/H1 subtypes)<br>Plus Internal Control and Type A M gene | | 40°C<br>25°C | H5N1 |
| Type A H1N1 (of H5/N1 subtypes)<br>Plus Internal Control and Type A M gene | | 40°C<br>25°C | H1N1 |
| Type A H3N2 (of H3 subtype)<br>Plus Internal Control and Type A M gene | | 40°C<br>25°C | H3N2 |
| Type A H5N2 (of H3 subtype)<br>Plus Internal Control and Type A M gene | | 40°C<br>25°C | H5N2 |
| Type A H3N1 (of H5/N1 subtypes)<br>Plus Internal Control and Type A M gene | | 40°C<br>25°C | H3N1 |
| Type A H1N2 (of H3 subtype)<br>Plus Internal Control and Type A M gene | | 40°C<br>25°C | H1N2 |
| Type A no detectable Type A HA or NA<br>Plus Internal Control and Type A M gene | | 40°C<br>25°C | Type A Virus<br>Serotype ? |
| Type A H5, no detectable NA<br>Plus Internal Control and Type A M gene | | 40°C<br>25°C | H5, no NA |
| Type A H1, no detectable NA<br>Plus Internal Control and Type A M gene | | 40°C<br>25°C | H1, no NA |
| Type A H3, no detectable NA<br>Plus Internal Control and Type A M gene | | 40°C<br>25°C | H3, no NA |
| Type A no detectable HA, N1 (of H5/N1 subtype) | | 40°C<br>25°C<br>40°C<br>25°C | |

FIGURE 16b (CONTINUED)

Plus Internal Control and Type A M gene                                         N1, no HA Type A no detectable HA, N2 (of H3 subtype)
Plus Internal Control and Type A M gene                                         N3, no HA

Probe Test Amplicon (H5N1), Tm=79.7
GTGGAGTAAAATTGGAATCAATAGGAATTTACCAAATACTGTCAATTTATTCTA
CAGTGGCGAGTTCCCTAGCACTGGCAATCATGGTAGCTGGTCTATCC Primer Amplicon (H5N1), Tm=77.2
GTGGAGTAAAATTGGAATCAATAGGAATTTACCAAATACTGTCAATTTATTCTA
CAGTGCACTGGCAATCATGGTAGCTGGTCTATCC Limiting Primer (reverse complement)
GGATAGACCAGCTACCATGATTGCC, Tm=<u>66.8 (H5N1),</u> 21.5(H3N2), 30.3 (H1N1), 14.2 (B)

Excess Primer-RNA 63.2 linear
GTGGAGTAAAATTGGAATCAATAGG, Tm=<u>63.6(H5N1),</u> 15.7(H3N2), 53.8(H1N1), 34.6(B)

Beacon Probe (reverse complement) Texas Red, Stem=58.1
Texas Red-CGCGACTAGGGAACTCGCTCGCG –Dabsyl, Tm=<u>52.7 (H5N1),</u> 8.0 (H3N2), 24.9(H1N1), 13.0(B)

2. H1

Probe Test Amplicon (H1N1), Tm=76.1
CCATGACTCCAATGTGAAGAATCTGTATGAGAAAGTAAAAAGCCAATTAAAGAA
TAATGCCAAAGAAATAGGAAACGGGTG Primer Amplicon (H1N1), Tm=73.5
CCATGACTCCAATGTGAAGAATCTGTATAAAGAATAATGCCAAAGAAATAGGAA
ACGGGTG Limiting Primer (reverse complement)
CACCCGTTTCCTATTTCTTTGGCATTATTC, Tm=22.5(H5N1), 21.6(H3N2), <u>66.7(H1N1),</u> 30.2(B)

Excess Primer, RNA 64.2 linear
CCATGACTCCAATGTGAAG, Tm=36.1(H5N1), 30.1(H3N2), <u>63.8(H1N1),</u> 20.3(B)

Beacon Probe (reverse complement) CY3, Stem=59.3
CY3-CGCGGATTGGCTTTTTACTTTCTCACCGCG-Dabsyl, Tm=7.8(H5N1), 20.1(H3N2), <u>56.6(H1N1),</u> 12.7(B)

Probe Test Amplicon (H5N1), Tm=87.4
GCAATAACTGATTGGTCAGGATATAGCGGGAGTTTTGTCCAGCATCCAGAACT GACAGGACTAGATTGCATAAGACCTTGTTTCTGGGTTGAGTTGATCAGAGGGC GGCCCAAAGAGAGCACAATTTGGACTAGTGGGAGCAGCATATCTTTTTGTGGT GTAAATAGTGACACTGTGGGTTGGTCTTGGCCAGACGGTGCTG

Primer Amplicon (H5N1), Tm=
GCAATAACTGATTGGTCAGGATATAGCGGGAGTTTTGTCCAGCATCCAGAACT GACAGGACTAGATTGCATAAGACCTTGTTTCTGGGTTGAGTTGATCAGAGGGC GGCCCAAAGAGAGCACAATTTGGACATCTTTTTGTGGTGTAAATAGTGACACTG TGGGTTGGTCTTGGCCAGACGGTGCTG

Limiting Primer (reverse complement)
CAGCACCGTCTGGCCAAGAC, Tm=69.3(H5N1), 69.3(H1N1), 41.0(H3N2), 5.7(B)

Excess Primer, RNA 66.3 linear
GCAATAACTGATTGGTCAGG, TM=62.9 (H5N1), 62.7(H1N1), 29.9(H3N2), 40.4(B)

Beacon Probe (reverse complement) FAM, Stem=63.6
FAM- GGCGGATGCTGCTCCCACTACCGCC -Dabsyl, Tm=56.3(H5N1), 56.3(H1N1), 12.1(H3N2), 25.8(B)

4. H3

Probe Test Amplicon (H3N2), Tm=78.0
CCATCAGATTGAAAAAGAATTCTCAGAAGTAGAAGGGAGAATTCAGGACCTCG AGAAATATGTTGAGGACACTAAAATAGATCTCTGGTCATACAACG

Primer Amplicon (H3N2), Tm=75.5
CCATCAGATTGAAAAAGAATTCTCAGAAGTAGAAGGGAGAATTTATGTTGAGG ACACTAAAATAGATCTCTGGTCATACAACG

Limiting Primer (reverse complement)
CGTTGTATGACCAGAGATCTATTTTAGTGTCCT, Tm=12.2(H5N1), 67.9(H3N2), 4.6(H1N1), -0.6(B)

Excess Primer, RNA 59.7 linear
CCATCAGATTGAAAAAGAATTCT, Tm=29.3(H5N1), 62.7(H3N2), 21.5(H1N1), 22.2(B)

EXO-R Probe (reverse complement) CY5, Stem=66.8

FIGURE 17 (CONTINUED)

CY5-CGCTGAAAGCGTTTCTCGAGGTCCTG-BHQ1, Tm=9.9(H5N1), <u>54.5(H3N2)</u>, 15.4(H1N1), 9.1(B)

4/5. B(HA)

Probe Test Amplicon, Tm=84.4
CGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACC
AAATATAGACCTCCTG Primer Amplicon, Tm=83.2
CGGTGGATTAAACAAAAGCAAGCCTTACTACGGCCATAGGAAATTGCCCAATA
TGGGTGAAAACACCCTTGAAGCTGGCCAATGGAACCAAATATAGACCTCCTG Limiting Primer (reverse complement)
CAGGAGGTCTATATTTGGTTCCATTGGC, Tm=14.4(H5N1), 21.0(H3N2), 24.8(H1N1), <u>67.5(B)</u>

Excess Primer, RNA 58.9 linear
CGGTGGATTAAACAAAAGCA, Tm=12.1(H5N1), 26.0(H3N2), 20.3(H1N1), <u>62.4(B)</u>

Beacon Probe 1 (reverse complement) Texas Red, Stem=54.0
Texas Red- GCGAGTTTGCATGTTCTCCTGTCTCGC -Dabsyl, Tm=19.2(H5N1), 16.2(H3N2), 15.3(H1N1), <u>52.1(B)</u>

Beacon Probe 2 (reverse complement) CY5, Stem=54.0
CY5- GCGAGTTTGCATGTTCTCCTGTCTCGC -Dabsyl, Tm=19.2(H5N1), 16.2(H3N2), 15.3(H1N1), <u>52.1(B)</u>

4/5. B(NA)

Probe Test Amplicon, Tm=83.3
CATGGGCTGACAGTGATGCCCTTGCTTTTAGTGGAGTAATGGTTTCAATGGAA
GAACCTGGTTGGTACTCCTTTGGCTTCGAAATAAAAGACAAGAAATGTGATGTC
CCCTGTATTGGG Primer Amplicon, Tm=
CATGGGCTGACAGTGATGCCCTTGCTTTTAGTGGAAGAACCTGGTTGGTACTC
CTTTGGCTTCGAAATAAAAGACAAGAAATGTGATGTCCCTGTATTGGG Limiting Primer (reverse complement)
CCCAATACAGGGGACATCACATTTCTTG, Tm=10.9(H5N1), 16.2(H1N1), -4.6(H3N2), <u>68.9(B)</u>

FIGURE 17 (CONTINUED)

Excess Primer, RNA 69.7 just linear
CATGGGCTGACAGTGAT, Tm=38.7(H5N1), 43.2(H1N1), 42.5(H3N2), <u>63.7(B)</u>

Beacon Probe 1 (reverse complement) Texas Red, Stem=58.1
Texas Red- GCCGCTCCATTGAAACCATTACGCGGC -Dabsyl, Tm=26.3(H5N1), 27.9(H1N1), 21.2(H3N2), <u>53.1(B)</u>

Beacon Probe 2 (reverse complement) CY5, Stem=58.1
CY5- GCCGCTCCATTGAAACCATTACGCGGC -Dabsyl, Tm=26.3(H5N1), 27.9(H1N1), 21.2(H3N2), <u>53.1(B)</u>

6. M

Probe Test Amplicon (H5N1) Tm=87.4
CTAACCGAGGTCGAAACGTACGTTCTCTCTATCATCCCGTCAGGCCCCCTCAAA
GCCGAGATCGCGCAGAAACTTGAAGATGTCTTTGCAGGAAAGAACACCGATCT
CGAGGCTCTCATGGAGTGGCTAAAGACAAGACCAATCCTGTCACC Primer Amplicon (H5N1), Tm=87.8
CTAACCGAGGTCGAAACGTACCATCCCGTCAGGCCCCCTCAAAGCCGAGATCG
CGCAGAAACTTGAAGATGTCTTTGCAGGAAAGAACACCGATCTCGAGGCTCTC
ATGGAGTGGCTAAAGACAAGACCAATCCTGTCACC Limiting Primer (reverse complement)
GGTGACAGGATTGGTCTTGTCTTTAGC, Tm=<u>67.3 (H5N1)</u>, <u>67.3(H3N2)</u>, <u>67.3(H1N1)</u>, 14.4(B)

Excess Primer
CTAACCGAGGTCGAAAC, Tm=<u>62.2(H5N1)</u>, <u>62.2(H3N2)</u>, <u>62.2(H1N1)</u>, 20.6(B)

Probe (reverse compliment) CY3, Stem=61.2
CY3- GCGCTATAGAGAGAACAGCGC -Dabsyl, Tm=<u>33.8 (H5N1)</u>, <u>33.8(H3N2)</u>, <u>33.8(H1N1)</u>, 9.6(B)

7. N2

Probe Test Amplicon (H3N2), Tm=80.6
GGTCCAACCCTAATTCCAAATTGCAGATAAATAGGCAAGTCATAGTTGACAGAG
GTAATAGGTCCGGTTATTCTGGTATTTTCTCTGTTGAAGGCAAAAGCTGCATC Primer Amplicon (H3N2), Tm=
GGTCCAACCCTAATTCCAAATTGCAGATAAATAGGCAAGTCATAGTTTTATTCT
GGTATTTTCTCTGTTGAAGGCAAAAGCTGCATC

FIGURE 17 (CONTINUED)

Limiting Primer (reverse complement)
GATGCAGCTTTTGCCTTCAACAGAG, Tm=29.4(H5N1), 16.7(H1N1), <u>67.4(H3N2)</u>, 15.6(B)

Excess Primer, RNA 69.4 just before hairpin
GGTCCAACCCTAATTCCAA, Tm=13.6(H5N1), 22.0(H1N1), <u>63.4(H3N2)</u>, 22.7(B)

Probe (reverse complement) FAM, Stem=61.2
FAM- GGCCGCCTATTACCTCTCGGCC -Dabsyl, Tm=30.0(H5N1), 27.7(H1N1), <u>38.9(H3N2)</u>, 20.6(B)

8. H3 Control

Probe Test Amplicon (H3N2), Tm=77.0
CCATCAGATTGAAAAAGAATTCTCAGAAGTAGAAGGGAGAATTCAGGAACTCT
AGAAATATGTTGAGGACACTAAAATAGATCTCTGGTCATACAACG Limiting Primer (reverse complement)
CGTTGTATGACCAGAGATCTATTTTAGTGTCCT, Tm=12.2(H5N1), <u>67.9(H3N2)</u>, 4.6(H1N1), -0.6(B)

Excess Primer
CCATCAGATTGAAAAAGAATTCT, Tm=29.3(H5N1), <u>62.7(H3N2)</u>, 21.5(H1N1), 22.2(B)

Probe (reverse complement) CY5, Stem=66.8
CY5- CGCTGAAAGCGTTTCTCGAGGTCCTG -BHQ1, Tm=32.9 vs. modified amplicon sequence CAGGAACTCTAGAAA

9. H5 Delete Region

Probe Test Amplicon(H5N1), Tm=79.0
CGACTGGGCTCAGAAATAGCCCTCAAAGAGAGAGAAGAAGAAAAAGAGAGGA
TTATTTGGAGCTATAGCAGGTTTTATAGAGGGAGG Primer Amplicon (H5N1), Tm=77.4
CGACTGGGCTCAGAAATAGCCCTCAAAGAGTTATTTGGAGCTATAGCAGGTTTT
ATAGAGGGAGG

FIGURE 17 (CONTINUED)

Limiting Primer (reverse complement)
CCTCCCTCTATAAAACCTGCTATAGCTCCAAA, Tm=69.7(H5N1), 14.3(H3N2), 20.5(H1N1), 6.5(B)

Excess Primer
CGACTGGGCTCAGAAA, Tm=62.9(H5N1), 17.4(H3N2), 29.3(H1N1), 17.4(B)

Probe Sequence(reverse complement), Stem Tm=
Fluor-stemTCCTCTCTTTTTTCTTCTTCTCTstem-Dabsyl, Tm=58.9(H5N1), -3.8(H3N2), 20.4(H1N1), 13.4(B)

DETECTION AND ANALYSIS OF INFLUENZA VIRUS

RELATED APPLICATIONS

This application claims the benefit under 35 U.S.C. §119 of U.S. provisional application No. 60/819,000, filed Jul. 7, 2006, which is hereby incorporated by reference in its entirety.

BACKGROUND

Rapid detection and typing of influenza virus and identification of its various strains is critical to identification and control of a potential human pandemic. Influenza virus is composed of eight single-stranded RNA molecules (HA, NA, PB2, PB1, PA, NS, M, NP) that code for eleven specific proteins. The RNA for the matrix protein (M) is relatively conserved and is therefore used to detect and distinguish a Type A virus. M can also be used to detect and distinguish H5N1.

The hemagglutinin protein (HA) and neuraminidase protein (NA) are grouped into 16 and 9 subtypes, respectively, both have high sequence variability even within subtypes and thus provide an effective means of monitoring changes that might occur in a virus. The HA protein protrudes from the surface of the virus and allows it to attach to a cell to begin the infection cascade. The NA protein is also located on the surface of the virus and allows the release of new particles within the infected cell.

Currently the Eurasian H5N1 virus infects only the lower lungs in human and is therefore less readily transmitted human-to-human than annual strains of human influenza that infect the upper respiratory track. But, mutations within the HA and NA RNAs are frequent and alter viral infectivity and lethality in different hosts and their tissues. In addition, gene assortment among the different viral subtypes is another very worrisome feature of influenza and could result in recombining RNA sequences for high infectivity in humans with high lethality.

SUMMARY

Accordingly, there is a need for an informative influenza assay that can be performed in the field, i.e., at the point of care ("POC"). Moreover, in order to save both time and money it will also be important to make POC assays compatible with more extensive laboratory analysis, such as sequencing of, for example, HA and NA. In this way, the evolution of a viral disease and viral genomics can be analyzed in real-time.

One embodiment is directed to an assay comprising a plurality of primer pairs, a plurality of probes, and a low copy number synthetic amplicon corresponding to each of the plurality of primer pairs.

BRIEF DESCRIPTION OF THE DRAWINGS

FIG. 2 is an agarose gel showing four sets of reactions, performed in triplicate, each reaction using the same Excess Primer (thick arrow), plus a different own Limiting Primer (thin arrow). The melting temperature of the four different Limiting Primers increases from left to right and the annealing temperature used for each set of reactions is 2° C. below the melting temperature of the Limiting Primer.

FIG. 5 shows reaction design (left panels) and dF/dT in the presence of SybrGreen (right panels) where five primer pairs and (a) one template or (b) one template corresponding to one primer pair+four low copy number amplicons corresponding to the remaining four primer pairs are included.

FIG. 11. LATE-PCR protocol with 50 nM limiting primer (LP) and 2 µM RT primer and LATE-PCR excess primer (XP).

FIG. 12 is a clustal comparison of Influenza Virus M RNA sequences for H3N2 (SEQ ID NO: 29), H5N1 (SEQ ID NO: 31), H1N1 (SEQ ID NO: 30), and B (SEQ ID NO: 32).

FIG. 13 is a clustal comparision of Influenza Virus HA RNA sequences for H3N2 (SEQ ID NO: 35), H5N1 (SEQ ID NO: 33), H1N1 (SEQ ID NO: 34), and B (SEQ ID NO: 36).

FIG. 14 is a clustal comparision of Influenza Virus NA RNA sequences for H3N2 (SEQ ID NO: 39), H5N1 (SEQ ID NO: 38), H1N1 (SEQ ID NO: 37), and B (SEQ ID NO: 40).

FIG. 15 shows a schematic of an embodiment of an assay

FIG. 16 shows the layout and an possible outcomes for an exemplary assay.

FIG. 17 provides primer, probe, and amplicon sequences that can be used in an embodiment of an influenza virus assay (SEQ ID NOS 41-42, 1-2, 19, 43-44, 3-4, 20, 45-46, 5-6, 21, 47-48, 7-8, 22, 49-50, 9-10, 23, 23, 51-52, 11-12, 24, 24, 53-54, 13-14, 25, 55-56, 15-16, 26, 57, 7-8, 22, 27, 58-59, 17-18 and 28, respectively, in order of appearance).

DETAILED DESCRIPTION

Figure 1:
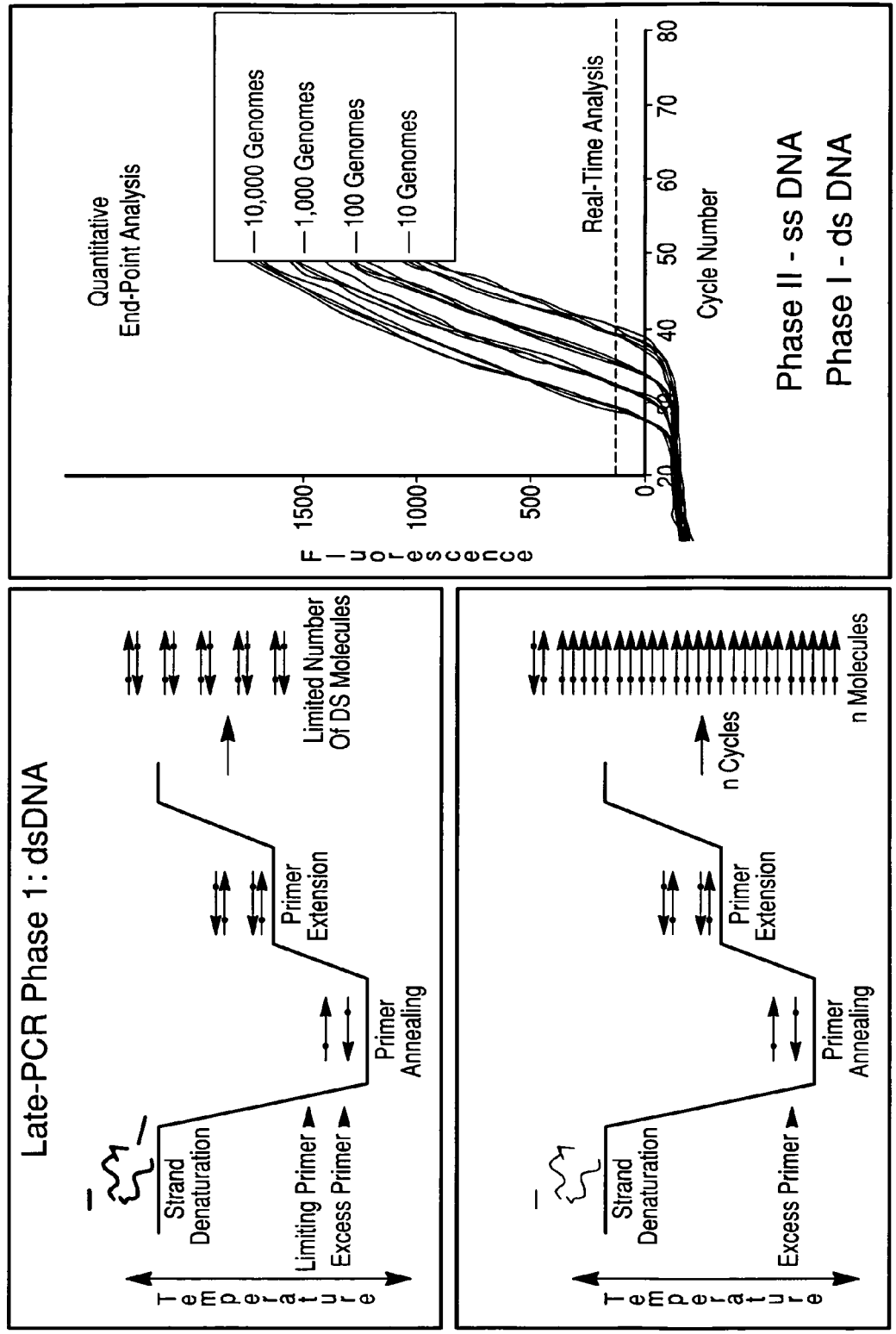
FIG. 1 illustrates an embodiment of LATE PCR (left) and provides fluorescence curves produced by LATE PCR.
Figure 3:
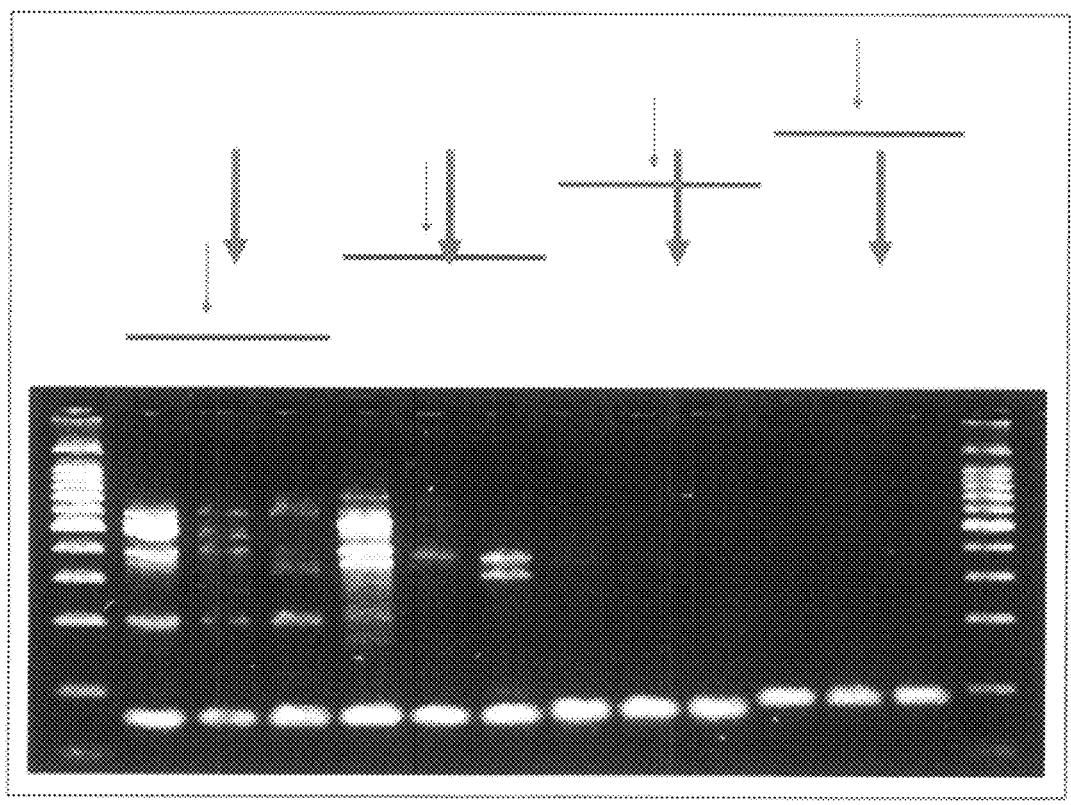
FIG. 3 shows agarose gels of identical LATE-PCR without ELIXIR (left) and with ELIXIR (right). The replicate reactions are prepared using four different preparations of commercially available Taq polymerases, both with and without a hot start. The reactions were incubated at room temperature for 30 minutes before amplification.
Figure 3:
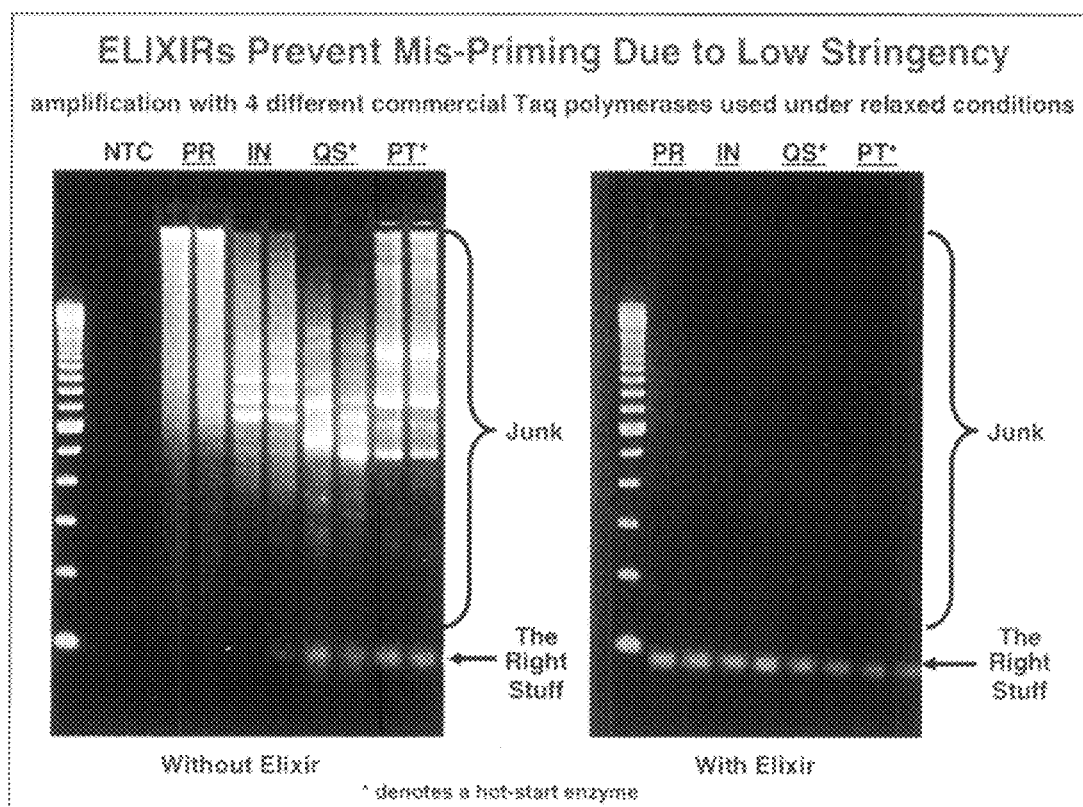
Figure 4:
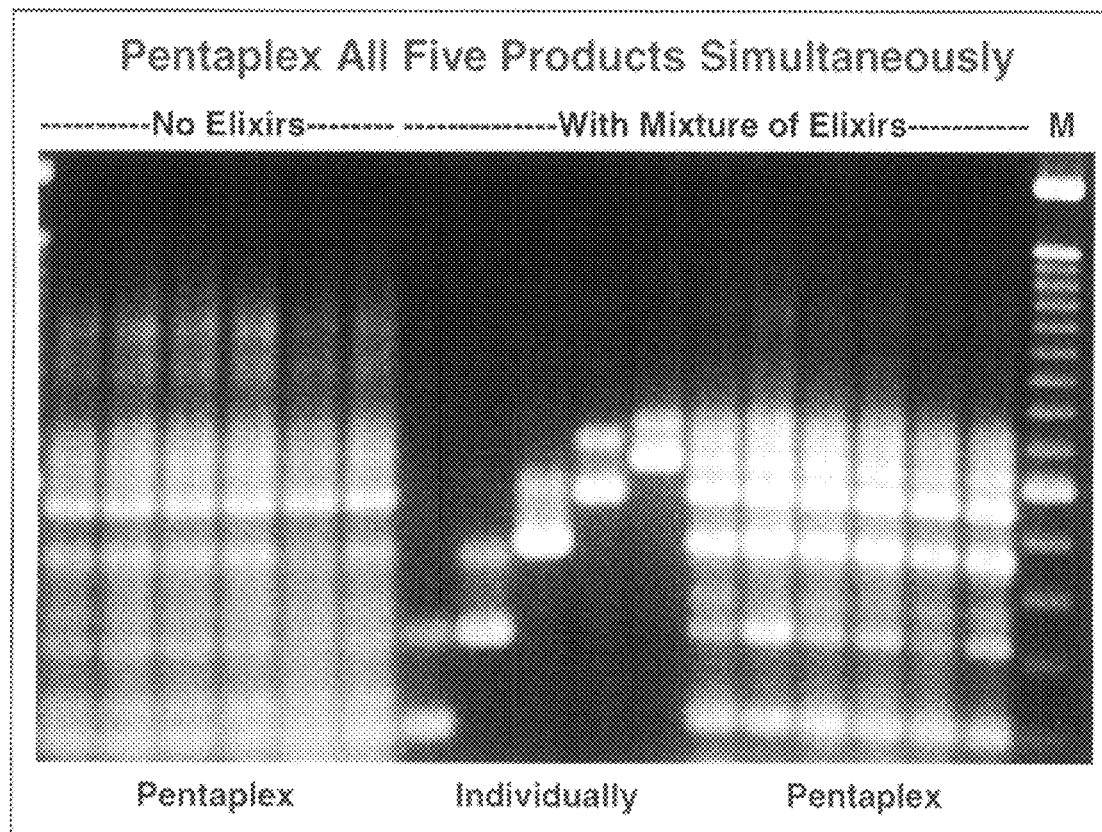
FIG. 4 is an agarose gel of a pentaplex LATE-PCR without ELIXIR (left six lanes), monoplex LATE-PCR with ELIXIR (middle five lanes), and pentaplex with ELIXIR (right six lanes). A molecular weight ladder is shown in far right lane. In the pentaplex reactions, all five targets are amplified simultaneously.

All references cited are incorporated herein by reference.

An influenza virus assay can detect and distinguish between various sub-types and strains of an influenza virus using any suitable nucleic acid amplification technique. This assay can be performed in a single reaction vessel with all reagents present at the start of an assay. An assay can use more than one primer pairs in combination with one or more probes to amplify and detect specific target nucleic acid sequences of influenza. Using the information obtained from an amplification reaction it is possible to distinguish between various sub-types and strains of the an influenza virus. Specifically, an assay can provide a positive or negative (yes/no) determination of the likely presence or absence of influenza virus types A and B, and sub-types H1N1, H3N2, and H5N1 in a sample. An assay also can be used to monitor for one or more mutations in an influenza virus strain. Mutations in an influenza virus, within, for example the HA and NA, can alter viral infectivity and lethality in different hosts and different tissues.

A sample can be any material to be tested, such as, for example, a biological or environmental sample. Biological samples can be obtained from any organism. In one embodiment, a sample is obtained from a mammal, such as a human, or a bird. In one embodiment, a sample comprises a nasopharyngeal aspirate, blood, saliva, or any other bodily fluid.

A nucleic acid amplification method used in an assay can be a thermal cycling technique, such as a polymerase chain reaction ("PCR") or an isothermal technique. Standard PCR amplification methods are described in, for example, U.S. Pat. Nos. 4,683,195 and 4,683,202 (both of which are incorporated herein by reference). In one embodiment, the nucleic acid amplification method is linear after the exponential ("LATE") PCR ("LATE-PCR"), as described in U.S. patent application Ser. No. 10/320,893, which is incorporated by reference. An embodiment of LATE-PCR is illustrated in FIG. 1. LATE-PCR is an asymmetric PCR method, which uses unequal concentrations of primers and can yield single-stranded primer-extension products, or amplicons. LATE-PCR amplifications and assays typically include at least 30 cycles, at least 60 cycles, or at least 70 cycles. FIG. 2, which shows an agarose gel showing that amplification product production is less specific when the melting temperature of the Limiting Primer is below that of the Excess Primer, demonstrates the specificity advantage that can be afforded by a properly designed LATE-PCR. An Excess Primer can misprime at a low annealing temperature, but the reaction can becomes very specific when the melting temperature of the Limiting Primer is above the melting temperature of the Excess Primer ($T_{mL[0]}-T_{mX[0]}\geqq 0$).

As used interchangeably herein, the terms "nucleic acid primer", "primer molecule", "primer", and "oligonucleotide primer" include short, (for example, between about 16 and about 50 bases) single-stranded oligonucleotides which, upon hybridization with a corresponding template nucleic acid molecule, serve as a starting point for synthesis of the complementary nucleic acid strand by an appropriate polymerase molecule. Primer molecules can be complementary to either the sense or the anti-sense strand of a template nucleic acid molecule. A primer can be composed of naturally occurring or synthetic oligonucleotides, or a mixture of the two. If the primers in a pair of PCR primers are used in unequal concentrations, as is the case in LATE-PCR, primer added at a lower concentration is a "Limiting Primer", and primer added at a higher concentration is an "Excess Primer."

As used herein "amplification target sequence" used interchangeably with "target sequence" and "target nucleic acid" refers to a DNA sequence that provides a template for copying by the steps an amplification technique. An amplification target sequence can be single-stranded or double-stranded. If the starting material is RNA, for example messenger RNA, the DNA amplification target sequence is created by reverse transcription of RNA to create complementary DNA, and the amplification target sequence is a cDNA molecule. Thus, in a PCR assay for RNA, a hybridization probe signals copying of a cDNA amplification target sequence, indirectly signifying the presence of the RNA whose reverse transcription produced the cDNA molecules containing the amplification target sequence. An amplification target sequence typically is bracketed in length by a pair of primers used to amplify it. An extension product (or amplicon), whether double-stranded or, in non-symmetric PCR, single-stranded, is the exponentially amplified amplicon, bracketed by the primer pair.

An amplification target sequence can be a single nucleic acid sequence. In some cases an amplification target sequence will contain allelic variations or mutations and, thus, will not be a single sequence, even though amplified by a single primer pair. An assay for an amplification target sequence containing variations may use one detection probe for all variations, a single allele-discriminating probe for one variant, or multiple allele-discriminating probes, one for each variant.

Any suitable primer pair can be used, such as, for example, one of more of the following primer pairs:

```
H5
Limiting Primer (reverse complement)
GGATAGACCAGCTACCATGATTGCC(SEQ ID NO: 1),
Tm = 66.8(H5N1), 21.5(H3N2), 30.3(H1N1), 14.2(B)

Excess Primer-RNA 63.2 linear
GTGGAGTAAAATTGGAATCAATAGG(SEQ ID NO: 2),
Tm = 63.6(H5N1), 15.7(H3N2), 53.8(H1N1), 34.6(B)

H1
Limiting Primer (reverse complement)
CACCCGTTTCCTATTTCTTTGGCATTATTC(SEQ ID NO: 3),
Tm = 22.5(H5N1), 21.6(H3N2), 66.7(H1N1), 30.2(B)

Excess Primer, RNA 64.2 linear
CCATGACTCCAATGTGAAG(SEQ ID NO: 4),
Tm = 36.1(H5N1), 30.1(H3N2), 63.8(H1N1), 20.3(B)

N1
Limiting Primer (reverse complement)
CAGCACCGTCTGGCCAAGAC(SEQ ID NO: 5),
Tm = 69.3(H5N1), 69.3(H1N1), 41.0(H3N2), 5.7(B)

Excess Primer, RNA 66.3 linear
GCAATAACTGATTGGTCAGG(SEQ ID NO: 6),
TM = 62.9(H5N1), 62.7(H1N1), 29.9(H3N2), 40.4(B)

H3
Limiting Primer (reverse complement)
CGTTGTATGACCAGAGATCTATTTTAGTGTCCT(SEQ ID NO: 7),
Tm = 12.2(H5N1), 67.9(H3N2), 4.6(H1N1), -0.6(B)

Excess Primer, RNA 59.7 linear
CCATCAGATTGAAAAAGAATTCT(SEQ ID NO: 8),
Tm = 29.3(H5N1), 62.7(H3N2), 21.5(H1N1),
22.2(B)

B(HA)
Limiting Primer (reverse complement)
CAGGAGGTCTATATTTGGTTCCATTGGC(SEQ ID NO: 9),
Tm = 14.4(H5N1), 21.0(H3N2), 24.8(H1N1), 67.5(B)

Excess Primer, RNA 58.9 linear
CGGTGGATTAAACAAAAGCA(SEQ ID NO: 10),
Tm = 12.1 (H5N1), 26.0(H3N2), 20.3(H1N1), 62.4(B)

B(NA)
Limiting Primer (reverse complement)
CCCAATACAGGGGACATCACATTTCTTG(SEQ ID NO: 11),
Tm = 10.9(H5N1), 16.2(H1N1),
-4.6(H3N2), 68.9(B)

Excess Primer, RNA 69.7 just linear
CATGGGCTGACAGTGAT(SEQ ID NO: 12),
Tm = 38.7(H5N1), 43.2(H1N1), 42.5(H3N2), 63.7(B)
```

-continued

```
M
Limiting Primer (reverse complement)
GGTGACAGGATTGGTCTTGTCTTTAGC(SEQ ID NO: 13),
Tm = 67.3(H5N1), 67.3(H3N2), 67.3(H1N1), 14.4(B)

Excess Primer
CTAACCGAGGTCGAAAC(SEQ ID NO: 14),
Tm = 62.2(H5N1), 62.2(H3N2), 62.2(H1N1), 20.6(B)

N2
Limiting Primer (reverse complement)
GATGCAGCTTTTGCCTTCAACAGAG(SEQ ID NO: 15),
Tm = 29.4(H5N1), 16.7(H1N1), 67.4(H3N2), 15.6(B)

Excess Primer, RNA 69.4 just before hairpin
GGTCCAACCCTAATTCCAA(SEQ ID NO: 16), labeled random coil probes are cut, or hydrolyzed, during the amplification reaction, and hydrolysis leads to a detectable signal change. Probes that rely on hydrolysis as part of signal generation are not probes that "signal upon hybridization."

In one embodiment, an assay uses a "molecular beacon probe," which is a single-stranded oligonucleotide, typically 25-35 bases-long, in which the bases on the 3' and 5' ends are complementary. Molecular beacon probes are discussed in, for example, U.S. Pat. Nos. 5,925,517, 6,037,130, 6,103,476, 6,150,097, and 6,461,817, and U.S. Patent Appl. Pub. No. 2004/0023269A1, all of which are incorporated by reference. A molecular beacon probe can form a hairpin structure at temperatures at and below those used to anneal the primers to the template (typically below about 60° C.). The double-helical stem of the hairpin brings a fluorophore attached to one end (often, but not necessarily the '5 end) of a probe in proximity to a quencher attached to the other end of the probe (typically, but not necessarily, the 3' end). In the hairpin configuration, probe fluorescence is quenched. If a probe is heated above the temperature needed to melt the double stranded stem apart, or a probe is allowed to hybridize to a target oligonucleotide that is complementary to a sequence within the single-strand loop of a probe, fluorophore and quencher are separated, and the resulting conformation shows increased fluorescence. The strength of a fluorescent signal can increases in proportion to the amount of a molecular beacon hybridized to an amplicon. Molecular beacons with different loop sequences can be conjugated to different fluorophores in order to monitor increases in amplicons that differ by as little as one base (Tyagi, S. and Kramer, F. R. (1996) "Molecular Beacons: Probes That Fluoresce Upon Hybridization," Nat. Biotech. 14:303-308; Tyagi, S. et al., (1998) "Multicolor Molecular Beacons for Allele Discrimination." Nat. Biotech. 16: 49-53; Kostrikis, L. G. et al., (1998) "Spectral Genotyping of Human Alleles," Science 279: 1228-1229).

Any suitable fluorophore/quencher pair can be used in a molecular beacon probe. In one embodiment, four probes are used each with a single fluorophore, wherein the flourophores are texas red, CY3, CY5, and FAM. Any suitable quencher can be used, such as, for example, Black Hole™ quenchers, dabsyl, and BHQ1. In one embodiment, an assay include one or more fluorophore/quencher pair, wherein the pair can be any of texas red/dabsyl, CY5/dabsyl, FAM/dabsyl, CY5/BHQ1, and CT3/dabsyl. In another embodiment, an assay uses one or more of the following probes:

```
H5
Texas Red-CGCGACTAGGGAACTCGCTCGCG(SEQ ID NO: 19)
-Dabsyl,
Tm = 52.7(H5N1), 8.0(H3N2), 24.9(H1N1), 13.0(B)

H1
CY3-CGCGGATTGGCTTTTTACTTTCTCACCGCG(SEQ ID NO: 20)
-Dabsyl,
Tm = 27.8(H5N1), 20.1(H3N2), 56.6(H1N1), 12.7(B)

N1
FAM- GGCGGATGCTGCTCCCACTACCGCC(SEQ ID NO: 21)
-Dabsyl,
Tm = 56.3(H5N1), 56.3(H1N1), 12.1(H3N2), 25.8(B)

H3
CY5-CGCTGAAAGCGTTTCTCGAGGTCCTG(SEQ ID NO: 22)
-BHQ1,
Tm = 9.9(H5N1), 54.5(H3N2), 15.4(H1N1), 9.1(B)

B(HA)
Beacon Probe 1
Texas Red- GCGAGTTTGCATGTTCTCCTGTCTCGC
(SEQ ID NO: 23)-Dabsyl,
Tm = 19.2(H5N1), 16.2(H3N2), 15.3(H1N1), 52.1(B)

Beacon Probe 2
CY5- GCGAGTTTGCATGTTCTCCTGTCTCGC
(SEQ ID NO: 23)-Dabsyl,
Tm = 19.2(H5N1), 16.2(H3N2), 15.3(H1N1), 52.1(B)

B(NA)
Beacon Probe 1
Texas Red- GCCGCTCCATTGAAACCATTACGCGGC
(SEQ ID NO: 24)-Dabsyl,
Tm = 26.3(H5N1), 27.9(H1N1), 21.2(H3N2), 53.1(B)

Beacon Probe 2 (
CY- GCCGCTCCATTGAAACCATTACGCGGC
(SEQ ID NO: 24)-Dabsyl,
Tm = 26.3(H5N1), 27.9(H1N1), 21.2(H3N2), 53.1(B)

M
CY3- GCGCTATAGAGAACAGCGC(SEQ ID NO: 25)
-Dabsyl, Tm = 33.8
(H5N1), 33.8(H3N2), 33.8(H1N1), 9.6(B)

N2
FAM- GGCCGCCTATTACCTCTCGGCC(SEQ ID NO: 26)
-Dabsyl,
Tm = 30.0(H5N1), 27.7(H1N1), 38.9(H3N2), 20.6(B)

H3 Control
CY5- CGCTGAAAGCGTTTCTCGAGGTCCTG(SEQ ID NO: 22)
-BHQ1,
Tm = 32.9 vs. modified amplicon sequence
CAGGAACTCTAGAAA(SEQ ID NO: 27)

H5 Delete Region
Fluor-stemTCCTCTCTTTTTTCTTCTTCTCTstem
(SEQ ID NO: 28)-Dabsyl,
Tm = 58.9(H5N1), -3.8(H3N2), 20.4(H1N1), 13.4(B)
```

In another embodiment, all of the above molecular beacon probes are used in an assay. In a further embodiment, an assay can include nine sequence-specific molecular beacons that are capable of detecting seven influenza virus targets. In a further embodiment, three molecular beacons probes, each detectable at a different wavelength, can form a probe-target hybrid at $T_m$ 45° C. and two additional molecular beacon probes, each detectable at a different single wavelength, can form a probe-target hybrid at $T_m$ 30° C. Further, two additional molecular beacon probes, each detectable a two different wavelengths, can form a probe-target hybrid at $T_m$ 45° C. An additional mis-match tolerant probe can also be used to detect one of the viral targets at 40° C. and a variant of that sequence present in an internal control at 25° C.

Figure 7:
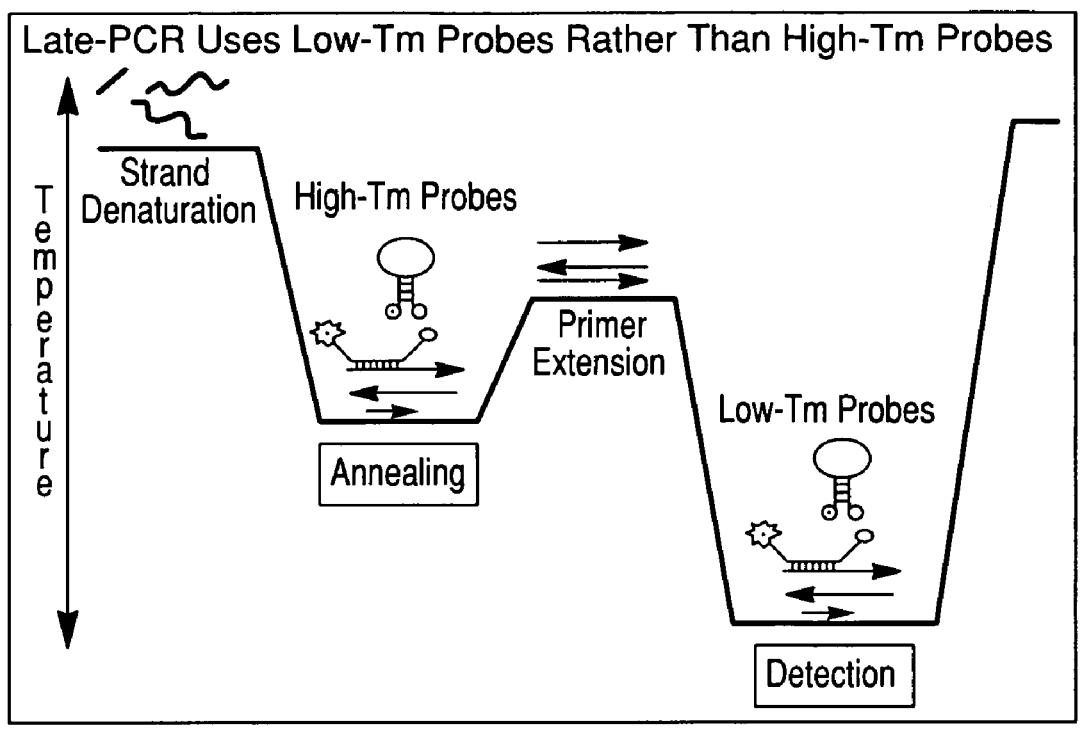
FIG. 7 shows an embodiment of a Low-$T_m$ Probe detection approach.

In one embodiment, an assays can use a "Low-$T_m$ Probe." A Low-$T_m$ Probe is discussed in U.S. patent application Ser. No. 10/320,893 and refers to a labeled hybridization probe that signals upon hybridization to its target, which in a LATE-PCR is the Excess Primer-Strand generated by extension of the Excess Primer, and that has a $T_{m[0]}^P$ at least 5° C. below or at least 10° C. below the $T_{m[0]}$ of the primer that hybridizes to and extends along the Excess Primer-Strand, which in a LATE-PCR is the Limiting Primer. FIG. 7 shows an embodiment of a Low-$T_m$ Probe detection approach.

Figure 8:
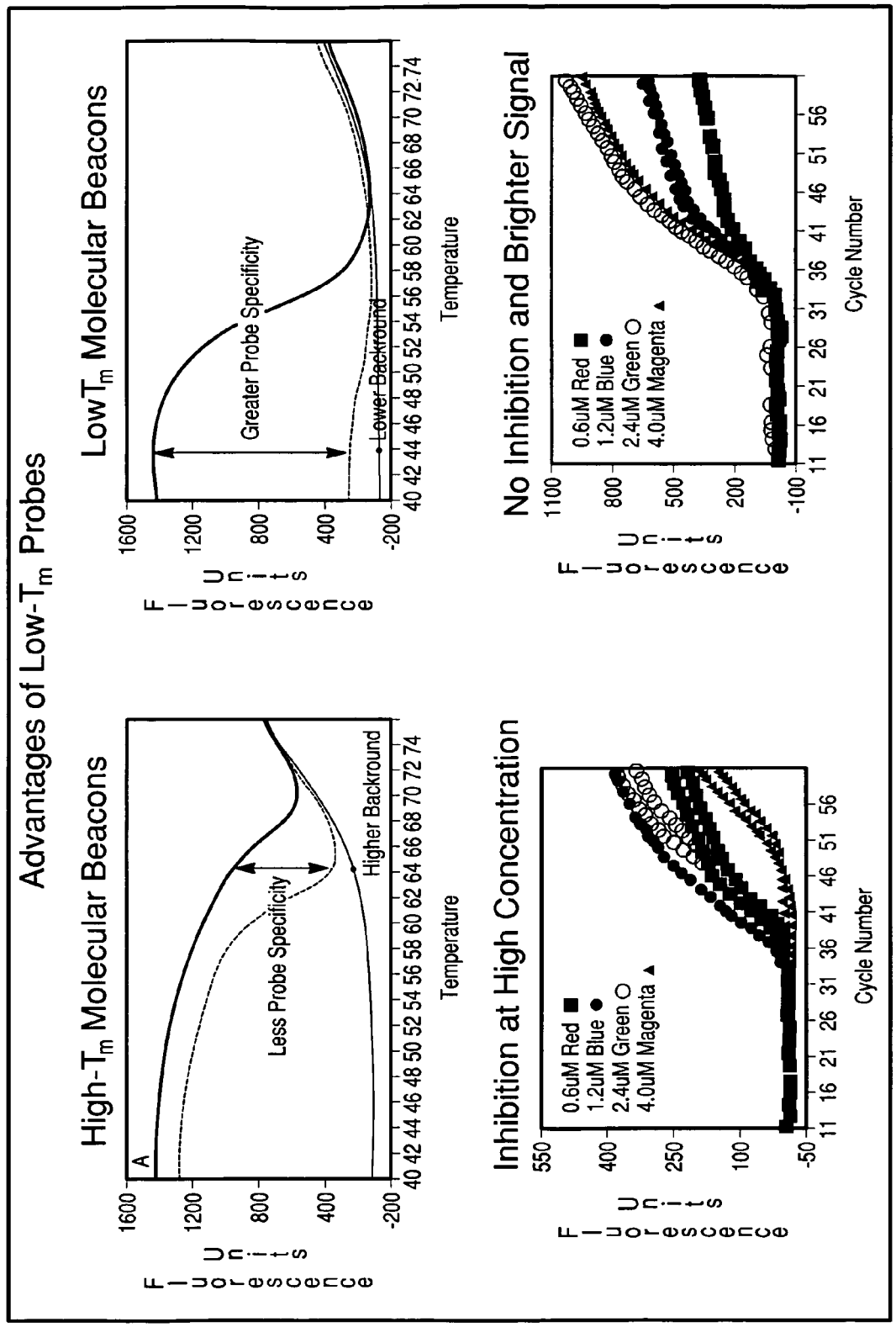
FIG. 8 compares amplification and detection of a high-$T_m$ molecular beacon probe and a low-$T_m$ molecular beacon probe.

As shown in FIG. 8, Low-$T_m$ Probes can be more specific over a wider temperature range and can display lower backgrounds. Low-$T_m$ Probes also show less amplification at higher concentrations than High-$T_m$ Probes.

In another embodiment, an assay can use a "Super-Low-$T_m$ Probe." This probe also is discussed in U.S. patent application Ser. No. 10/320,893.

An assay can include more than one probe. In one embodiment, multiple molecular beacon probes are used. In another embodiment, the probes are capable of forming probe-target hybrids are more than one temperature. In a further embodiment, multiple probes can be used, where a first probe forms a probe-target hybrid at a first temperature and a second probe forms a probe-target hybrid at a second temperature. In one embodiment, five molecular beacon probes can form a probe-target hybrid at a temperature of greater than 45° C. and can be detected at 40° C. and two molecular beacon probes can form a probe-target hybrid at 30° C. and can be detected at 25° C.

Figure 9:
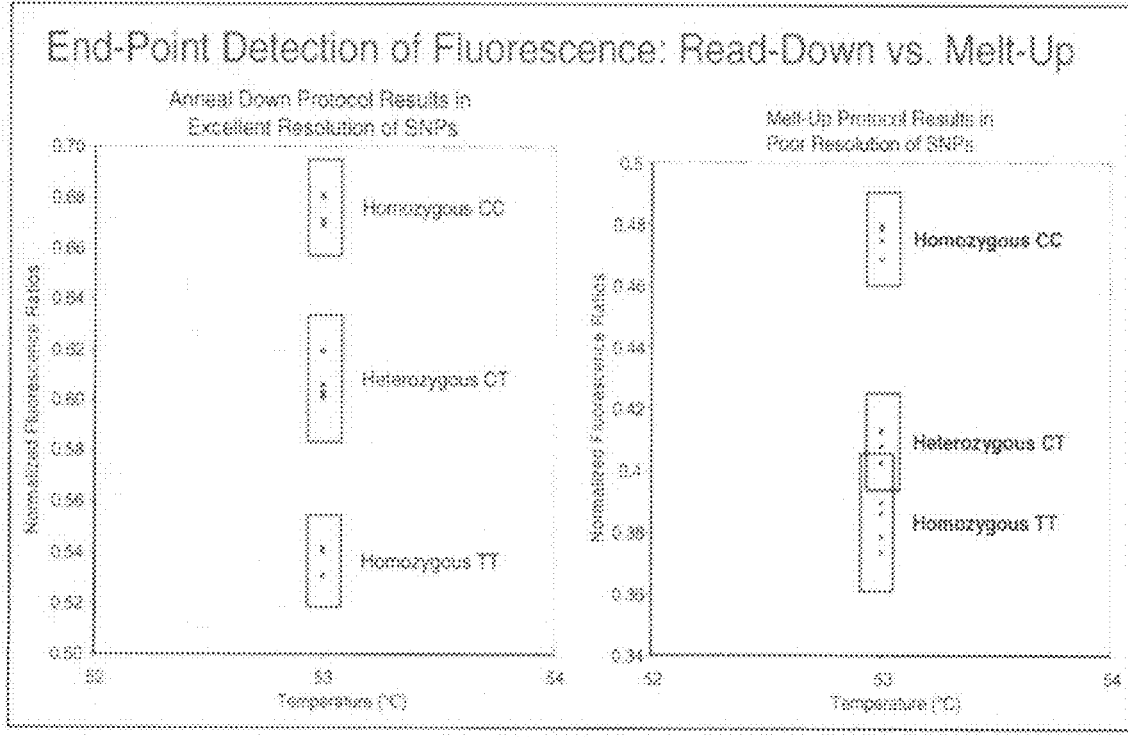
FIG. 9 compares resolution of single nucleotide polymorphism in heterozygous CC, heterozygous CT, and homozygous TT using an anneal down protocol (left) and a melt-up protocol (right).
Figure 10:
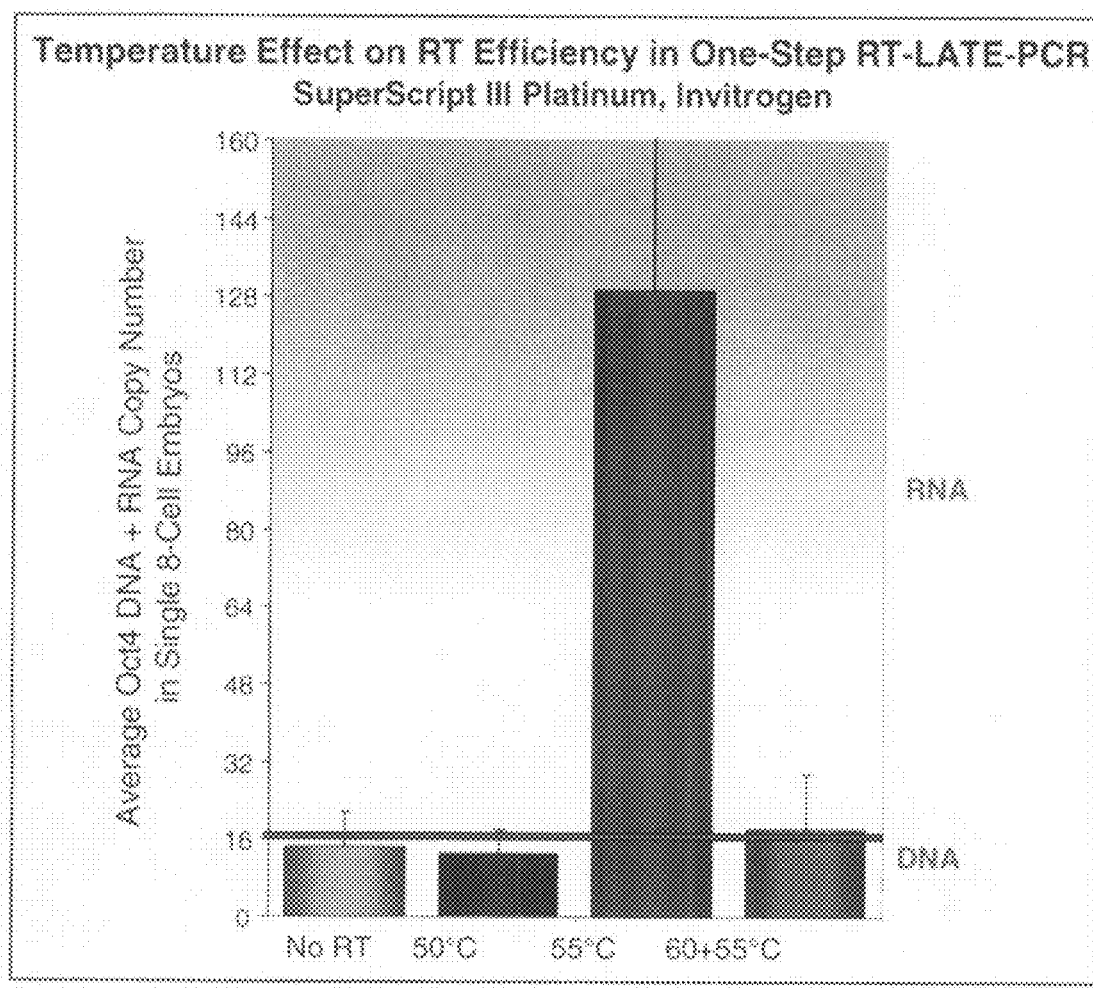
FIG. 10. LATE-PCR The captions under the bars indicate the temperature used for RT prior to LATE-PCR. No RTase (light blue bar), the inactivated RTase (blue bar), 30 min at 50° C. (green bar), 30 min at 55° C.; 10 min at 60° C.+20 min at 55° C. (orange bar). LATE-PCR is identical for all samples.

An assay can also include mismatch tolerant probes, such as, for example, fluorescent probes. In one embodiment, an assay uses a mismatch tolerant probes. An assay also can detect probe-target hybrids as a sample is cooled after PCR amplification ("anneal down"). This approach can be used in end-point fluorescence detection. This anneal-down approach can be more sensitive and provide better resolution than cooling first and then reading during warm-up (melt-up), because the read-during-cooling approach can minimize formation of hairpin structures in a target sequence. FIG. 9 compares resolution of single nucleotide polymorphism in heterozygous CC, heterozygous CT, and homozygous TT using an anneal down protocol (left) and a melt-up protocol (right). In one embodiment, the temperature of an assay reaction is changed from less than 95° C. to less than 65° C. than 45° C., to less than 25° C.

An influenza viral assay (or an assay of any RNA virus) can involve reverse transcription (RT) as a first step of a detection reaction. During reverse transcription RNA sequences are converted to complementary DNA (cDNA), providing a cDNA template for PCR amplification.

An approach to RT-PCR is the use of a "One-Step RT-PCR system." In a system of this type, reagents for both RT and PCR can be added to a sample in a single mixture and the reaction tube can be sealed and placed in a thermocycler. The RT and PCR enzyme-catalyzed reactions are carried out sequentially in the thermocycler, taking advantage of the different thermostabilities of the enzymes involved (typically, a reverse transcriptase and a thermostable DNA polymerase) and by setting an appropriate thermal profile. An initial incubation at non-denaturing temperature allows RT to occur first. The temperature then can be raised to initiate PCR; at this temperature, the reverse transcriptase can be inactivated, but the DNA polymerase is not. When a "hot start" is used, DNA polymerase is kept inactive during the RT step by interaction with a specific antibody. When the temperature is elevated, the antibody can be denatured and the DNA polymerase activated. In one embodiment, a multi-functional enzyme, having both a RTase activity and a DNA polymerase activity, can be used. In a further embodiment, a multi-functional enzyme having RTase activity, DNA polymerase activity, and exonuclease activity can be used, where the exonuclease activity can cleave double-stranded DNA in TaqMan-type detection method.

The temperature and duration of RT and PCR steps can be readily determined by one of skill in the art. In one embodiment, an RT step can be performed for from less than 2 minutes to more than 60 minutes at a temperature of from approximately 50-60° C. and a DNA-polymerase step can be performed as a thermocycle at approximately 95° C. for several cycles as discussed elsewhere.

An assay can be performed using any suitable device, such as a thermal cycler. In one embodiment, an assay is performed using a portable device, a man-portable device, or a handheld device, such as, for example, a Bioseeq II. In another embodiment, an assay is performed using a bench-top device, including, for example, an ABI Prism 7700 Sequence Detector (Applied Biosystems, Inc., CA) machine, a Cepheid Smart Cycler, and a Primus PCR thermocycle.

An assay can be performed in less than or equal to 30 minutes, less than or equal to 20 minutes, less than or equal to 15 minutes, or less than or equal to 10 minutes.

Assay reagents can be provided as a kit or a consumable. The reagents can be supplied as a lyophilized preparation. Each reagent can be supplied separately or as a mixture of one or more reagents. Reagents also can be supplied on a substrate, such as a bead. A lyophilized reagent can be stable for more than one year.

Figure 6:
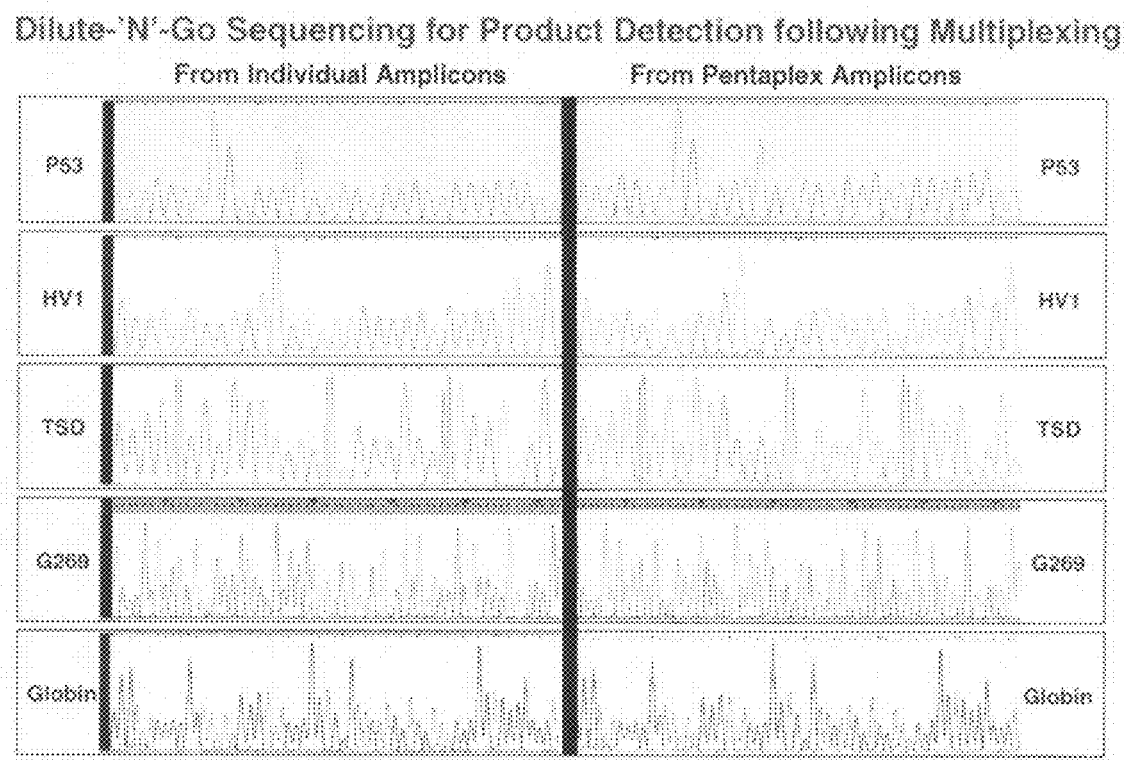
FIG. 6 shows pyrosequencing of a LATE-PCR monoplex reaction (left panel) and a multiplex reaction (right panel). The post-LATE-PCR reactions are split into five aliquots each and pyrosequencing performed in the presence of a sequencing primer corresponding to each amplicon.

An assay can yield single-stranded products for further use, for example as starting material for DNA sequencing or as probes in other reactions, or can be used in other assays. In one embodiment, single stranded DNA produced by an assay (assay product) can be sequenced using any suitable sequencing method, such as, for example, the dideoxy-method or pyrosequencing (Salk et al. (2006) Anal. Biochem. 353:124, incorporated by reference) by diluting a fraction of the assay reaction products into a sequencing reaction mixture. Assay product can be diluted by approximately 1:10, approximately 1:20, approximately 1:50, approximately 1:100, or approximately 1:200 or more for use in a sequencing reaction. FIG. 6 shows a LATE-PCR multiplex reaction, in which one sample is split into five aliquots each spiked with a different sequencing primer, and sequenced.

An assay can distinguish Influenza Type B and Type A virus. In one embodiment, an assay distinguishes Influenza Type B and Type A virus on the basis of sequences in the HA and NA genes. Within the Type A viruses an assay can distinguish between subtypes H5 (with or without N1 or N2), H1 (with or without N1 or N2), and H3 (with or without N1 or N2). In one embodiment, an N1 target sequence used is conserved for the H5 and H1 subtypes and can be useful for detecting H5N1 and H1N1. In another embodiment, H3N1 can be determined and such a determination can indicate viral reassortment. The N2 target sequence used is characteristic of the H3N2 subtype, thus, detection of H5N2 or H1N2 can indicate viral reassortment. FIGS. 12-14 shows clustal comparisons of influenza virus M, HA, and NA proteins for virus H1N1, H5N1, H3N2, and B. Such analysis is useful in interpreting data obtained from an assay and from subsequent sequencing of assay products. Using information obtaining from an assay, it is possible to monitor mutations in a known virus strain, which allows for detection of and prediction of changes in virulence and infectivity.

An exemplary avian influenza assay and possible results of this exemplary assay are provided in Table I and FIG. 15. FIG. 16 shows a schematic of an embodiment of an assay and FIG. 17 provides primer, probe sequences, and amplicon sequences that can be used in an embodiment of an influenza virus assay. In one embodiment, an assay include all of the primers and probes of FIG. 17 in a mono-multiplex assay. The features of such a mono-multiplex are summarized in Table I and the 15 possible outcomes of the reaction are illustrated 16.

TABLE I

| Position | Amplicon Primers | Target Sequence | Probe Type | Color(s) | Melting Tm |
|---|---|---|---|---|---|
| 1 | H5 | H5 | M. Beacon | Red | 45 C. |
| 2 | H1 | H1 | M. Beacon | Yellow | 45 C. |
| 3 | N1 | N1 | M. Beacon | Green | 45 C. |
| 4 | H3 | H3 | EXO-R | Blue | 45 C. |
| 6 | Type A M gene | M gene | M. Beacon | Yellow | 30 C. |
| 7 | N2 | N2 | M. Beacon | Green | 30 C. |
| 4/5 | Type B HA only | Type B HA only | M. Beacon | Blue | 45 C. |
|  | Type B HA only | Type B HA only | M. Beacon | Red | 45 C. |
| 4/5 | Type B NA only | Type B NA only | M Beacon | Blue | 45 C. |
|  | Type B NA only | Type B NA only | M. Beacon | Red | 45 C. |
| 4/5 | Type B HA + NA | Type B HA + NA | M Beacon | Blue + Blue | 45 C. |
|  | Type B HA + NA | Type B HA + NA | M. Beacon | Red + Red | 45 C. |
| 8 | H3 int. control | mis-matched H3 | EX0-R | Blue | 30 C. |
|  | H5 int. control | no matches | no probe |  |  |
|  | H1 int. control | no matches | no probe |  |  |
|  | N1 int. control | no matches | no probe |  |  |
|  | N2 int. control | no matches | no probe |  |  |
|  | M int. control | no matches | no probe |  |  |
|  | Type B HA i.c. | no matches | no probe |  |  |
|  | Type B NA i.c. | no matches | no probe |  |  |

The exemplary assay described in this table contains:
8 pairs of primers
3 Molecular Beacons with 45° C.
2 Molecular Beacons with 30° C.
2 pairs of Molecular Beacons both at 45° C.
Total = 9 Molecular Beacons
1 mismatch-tolerant prove
1 detectable internal control
7 undetected internal controls

EXAMPLE 1

Starting with samples of purified RNA, the HA RNA (1770 nucleotides long) and the NA RNA (1400 nucleotides long) are both be reverse transcribed in toto using random hexamers in a highly efficient two step RT-procedure. Each reaction also contains low levels of an M-Gene control DNA. The resulting control and cDNA molecules are amplified in two parallel multiplex LATE-PCR assays that each generate six amplicons. The presence of Eurasian H5N1 strain in a sample is established by probing for M, N1 and two different H5 sequences that are likely to be crucial for human-to-human transmission and for virulence. Reactions that do not generate either signal for H5 Eurasian will nevertheless produce a control DNA signal, proving that they are not false negatives. Reactions that do signal the presence of the H5 Eurasian strain from either of two independent probes (one in Multiplex A and one in Multiplex B) also generates a strong M-gene signal in both Multiplex A and Multiplex B. However, some samples may generate a signal for an M protein and only one of two possible HA signals. This is regarded as an indication of viral evolution. All samples that generate either one or two HA signals, or an N1 signal plus an M-gene signal are immediately be processed further for analysis. The amplicons for the all portions of HA and NA already are present in the LATE-PCR multiplex reactions. All 10 HA and NA amplicons are 300-500 bp in length and are processed for parallel pyrosequencing sequencing.

EXAMPLE 2

This example is directed to an RT-LATE-PCR assay for the quantification of Oct4-specific sequences in embryonic mouse cells. Oct4 is a gene expressed in totipotent and pluripotent cells and, therefore, preimplantation embryos contain considerable levels of Oct4 RNA. In addition, each cell contains two copies of the Oct4 gene (Oct4 genomic DNA). In the experiments presented in this example, Oct4 RNA and DNA are co-purified and co-quantified, according to a method previously published by this laboratory (Hartshorn C, Anshelevich A, Wangh L J. Rapid, single-tube method for quantitative preparation and analysis of RNA and DNA in samples as small as one cell. BMC Biotechnol 2005; 5:2.). Briefly, single embryos at the 8-cell stage are transferred to tiny droplets of dry lysing reagents placed on the lid of PCR tubes. After cell lysis, which occurs very rapidly, the tube is placed on the lid and inverted. One-step RT-PCR is performed by adding the reagents in the same tube already containing the lysed sample. Thus, both RNA and DNA are present in each sample. LATE-PCR primers are designed within an exon, also according to our published strategy, so that amplicons generated by Oct4 cDNA molecules and Oct4 genomic DNA molecules are identical and detected by the same fluorescent probe, a sequence-specific molecular beacon conjugated to the TET fluorescent dye. The final volume of these assays is 50 μl, according to the instruction of the One-Step RT-PCR kit, but the volume can be decreased to 25 μl.

The RT-LATE-PCR reaction is carried out in an ABI Prism 7700 Sequence Detector (Applied Biosystems, CA) and quantification of "total DNA" (cDNA+genomic DNA) copy numbers for each sample is achieved by comparison with standard scales prepared with serial dilutions of commercially available genomic DNA. (Because the Oct4 primers are designed to amplify equally cDNA and genomic DNA, standard scales of genomic DNA are amplified exactly with the same efficiency as unknown cDNA samples, ensuring accurate quantification.) The total number of Oct4 templates in each 8-cell embryo includes 16 copies of genomic DNA (two copies of the gene per cell, one on each chromosome 17) while all the other copies are due to the presence of cDNA and, thus, reflect the Oct4 RNA content of the embryo.

Several One-Step RT-PCR kits are tested using this assay and the efficiencies for Oct4 RNA quantification are compared. FIG. 10 shows the effect of temperature on SuperScript III reverse transcriptase (Invitrogen).

The blue and orange bars in the figure are comparable to the light blue "No RT" bar, indicating that under these temperature conditions RT does not take place and only genomic Oct4 DNA is amplified in the samples (16 copies per embryo, as expected). At 55° C. (green bar), however, RT occurs and cDNA is efficiently generated. Considering that the reverse transcriptase used for these experiments is active in the 42-60° C. range, this narrow window of activity is unexpected. To clarify this point, the thermodynamics of the Oct4 primers during RT is analyzed and compared to their behavior during PCR.

Visual OMP 5.0 software(VOMP) is used for this analysis and the results are summarized in FIG. 11. The two primers used for a LATE-PCR assay (limiting primer, LP, and excess primer, XP) have different $T_m$s and concentrations. In the Oct4 RT-LATE-PCR assay the most abundant primer (XP) is also the RT primer, being antisense to Oct4 RNA. As shown in FIG. 11, the effective $T_m$ of this primer calculated in the presence of double-stranded DNA during the PCR annealing step (at 55° C.) is of 66° C., very close to the calculated $T_m$ of 67° C. The effective $T_m$ of this same primer, however, drops dramatically to 53° C. in the presence of single-stranded RNA, even if the temperature of RT is also set at 55° C. This change results in a much lower percent of primer hybridized during RT than during the PCR annealing step, although the temperature is the same during the two steps. Although only 50% of the available primer is hybridized to target at 55° C., the primer was present at high concentration (2 μM) which allowed efficient RT. Additional VOMP analyses show that Oct4 XP's effective $T_m$ during RT does not change in the 50-60° C. range, which explains why increasing RT temperature in this case led to RT failure (much less primer was bound to target at 60° C. than at 55° C. and, contrary to the manufacturer's indications, the RTase was completely denatured after the initial 10 minutes at 60° C., see next section). On the other hand, the failure of RT at temperature lower than 55° C. (when, based solely on $T_m$, more primer should be hybridized) is probably due to increased levels of secondary structure of the target RNA interfering with the ability of the reverse transcriptase to progress along the template strand.

These results indicate that primers designed for PCR or LATE-PCR also should be analyzed in terms of their thermodynamic modification of a primer's design so that its $T_m$ can meet the necessary requirements during both RT and PCR. In cases where this is not possible due to restraints intrinsic to the sequence, a third primer—designed to hybridize only during the RT step—could be added to the one-step mixture. In addition, the characteristics of LATE-PCR are advantageous to promote RT priming in a one-step assay. In fact, by designating the XP to be also the RT primer we are able to use higher RT primer concentrations than those used under standard conditions in RT-PCR assays.

EXAMPLE 3

This example demonstrates optimization of RT reaction parameters.

Satisfactory RT results are obtained for two different genes shortening the RT step from 30 to 5 minutes, although a slight loss of sensitivity is observed. Further reducing RT to 2 or 3 minutes still yields acceptable results. The reverse transcriptase used was SensiScript by Qiagen. (Raja et al., 2002. Temperature-controlled Primer Limit for Multiplexing of Rapid, Quantitative Reverse Transcription-PCR Assays: Application to Intraoperative Cancer Diagnostics. Clinical Chemistry 48:8, 1329-1337.)

RT also performed with SuperScript II (Invitrogen) for 5 minutes. (Raja et al., 2005. Technology for Automated, Rapid, and Quantitative PCR or Reverse Transcription-PCR Clinical Testing. Clinical Chemistry 51:5, 882-890.)

RT is successfully carried out for just 1 minute with either MMLV (Moloney Murine Leukemia Virus RT) or SuperScript III (Stanley and Szewczuk, 2005. Multiplexed tandem PCR: gene profiling from small amounts of RNA using SYBR Green detection. Nucleic Acids Research 33:20, e180.)

Based on the above studies, a One-Step RT-PCR assay for detection of avian flu is designed that will encompass a RT step of no more than 5 minutes and as low as 1 minute. In doing so, we are aware that the optimal length of the RT reaction depends on several factors, including, but not limited to, efficient primer binding (see Example 2). The intrinsic thermostability of the RT enzyme also comes into play when choosing the temperature for RT, because the half-life of any enzyme sharply decreases at increasing temperatures, although some enzymes are more stable than others.

A clear example is provided by the following table posted on the web by the manufacturer Invitrogen
Summary of RT Half lives at 50, 55, and 60° C.

| Temperature | Superscript ™ II RT (min) | Superscript ™ III RT (min) |
|---|---|---|
| 50° C. | 6.1 | 220 |
| 55° C. | 2.2 | 24 |
| 60° C. | ND | 2.5 |

From this table it follows that, when working with SuperScript III at 60° C. or with SuperScript II at 55° C., the optimal RT step duration is no more than 5 minutes in any case, independently from the primer $T_m$s, because the enzyme is completely denatured in this period of time.

Newer RTases with broader thermostability ranges are commercially available. For example, StrataScript 5.0 from Stratatgene, has a half-life of 35 minutes at 55° C. There is also a number of polymerases commercialized by Roche and derived from thermophilic bacteria, which have both RTase and DNA polymerase activity.

We note that it is important to designing gene-specific RT primers with $T_m$s precisely calculated for optimal hybridization to target at a temperature elevated enough to minimize the secondary structure of single-stranded, GC-rich RNA molecules such as those present in viral genomes, but at the same time allowing a sufficient half-life of the chosen enzyme. The importance and the subtleties of this approach are not widely recognized, as shown by the suggestion: "Primers for real-time RT-PCR should be designed according to standard PCR guidelines" (Platinum Quantitative RT-PCR ThermoScript One-Step System instruction sheet, included with product purchased in 2006).

EXAMPLE 4

This example demonstrates the use of a Smiths Detection Bio-Seeq II instrument as a portable, point-of-care assay device. The Bio-Seeq II used in this example is comprised of four independently operating thermal cycling units, each encasing a long thin-walled sample tube having a sample volume of 25 ul. The primers and probes provided in FIG. 17 are used. Each sample is viewed using four-color fluorescence optics for dyes that emit at 520 nm, 580 nm, 625 nm, 680 nm. All colors can be viewed simultaneously without moving parts, a feature of the BioSeeq that reduces sampling time and lowers the risk of mechanical failure. To make full use of the broad detection temperature range available in LATE-PCR each unit can ramp up at 10° C./sec between 25-95° C., and is actively cooled at a rate of at least 2.5° C./sec between 95-25° C. The tolerance for thermal variance at any chosen hold temperature is ±1° C. The unit is AC or battery powered.

Each of the LATE-PCR mono-multiplex assays described below is designed to detect and distinguish any one of 15 possible outcomes in a single closed-tube. See FIGS. 15 and 16. These assays are easy to use "in the field" and provide rapid definitive yes/no answers as to the absence or presence of Influenza Virus sub-types H1N1, H3N2, B and H5N1. The assays also detect the presence of a Type B virus, or Type A influenza virus of unknown sub-type and include internal controls to rule out false negatives.

Each mono-multiplex reaction includes internal control target sequences, as shown in FIG. 17, at low copy number (approximately 20) to insure that all primer pairs are engaged in amplifying either a viral target sequence or an internal control. Accordingly, the reaction described below utilizes eight pairs of primers and eight internal controls.

Each mono-multiplex reaction is read at end-point by dropping the temperature to 40° C. and then to 25° C. Nine sequence-specific molecular beacons are used in this reaction to detect 7 of the possible viral targets. Three molecular beacons, each of a single color, form probe-target hybrids at Tm 45° C. Two additional molecular beacons, each of a single color, form probe-target hybrids at Tm 30° C. Two additional molecular beacons, each with two colors, form probe-target hybrids at Tm 45° C.

One mis-match tolerant probe is used to detect one of the viral targets at 40° C. and a variant of that sequence present in an internal control at 25° C. Seven of eight internal controls go undetected because they possess no targets for any probe.

Each mono-multiplex reaction is designed to distinguish Influenza Type B and Type A viruses on the basis of sequences in the HA and NA genes. Within the Type A viruses the reaction distinguishes between subtypes H5 (with or without N1 or N2), H1 (with or without N1 or N2), and H3 (with or without N1 or N2). The N1 target sequence used is conserved for the H5 and H1 subtypes and therefore is useful for detecting H5N1 and H1N1. Detection of H3N1 would indicate viral reassortment. The N2 target sequence used is characteristic of the H3N2 subtype. Therefore detection of H5N2 or H1N2 would indicate viral reassortment. The mono-multiplex reaction described here is a one-step RT-LATE-PCR reaction. The chemical features of this one-step process are described elsewhere.

One assay provides a reliable means of detecting the Eurasian subtype of H5. Specimens that test positive for H5 Eurasian in the field are be sent to an analytical laboratory for complete multiplex analysis and sequencing.

In a second assay, the H5 amplicon produced in the field includes the region of the RNA known to code for high pathogenicity of the Eurasian sub-type. This region is less conserved, but very important. Under these circumstances the tube that tests positive in the field for Eurasian H5 is sent to the laboratory for immediate sequencing of the H5 amplicon. There is no need to transport the specimen itself or additional amplification The next step involves in-depth laboratory analysis of influenza genes using LATE-PCR multiplexing and nucleic acid sequencing. Starting with samples of purified RNA, the HA RNA (1770 nucleotides long) and the NA RNA (1400 nucleotides long) are both be reverse transcribed in toto using random hexamers in a highly efficient two step RT-procedure. Each reaction also contains low levels of the same M-Gene control DNA describes for the BioSeeq POC assays above. The resulting control and cDNA molecules are amplified in two parallel multiplex LATE-PCR assays that each generate six amplicons (FIG. 15).

The possible presence of Eurasian H5N1 strain in a sample will be established by probing for M, N1 and two different H5 sequences which are likely to be crucial for human-to-human transmission and for virulence. Reactions that do not generate either signal for H5 Eurasian still produce a Control DNA signal, proving that they are not false negatives. Reactions that do signal the presence of the H5 Eurasian strain from either of two independent probes (one in Multiplex A and one in Multiplex B) also generate a strong M-gene signal in both Multiplex A and Multiplex B. However, some samples may generate a signal for the Matrix protein and only one of the two possible HA signals. This is regarded as an indication of viral evolution. All samples that generate either one or two HA signals, or an N1 signal plus an M-gene signal will immediately be processed further for analysis. Amplicons for the all portions of HA and NA are already be present in the LATE-PCR multiplex reactions. All 10 HA and NA amplicons are 300-500 bp in length and are processed for parallel pyrosequenceing as described above.

SEQUENCE LISTING

<160> NUMBER OF SEQ ID NOS: 59

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggatagacca gctaccatga ttgcc                                            25

<210> SEQ ID NO 2
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
gtggagtaaa attggaatca atagg                                           25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacccgtttc ctatttcttt ggcattattc                                      30

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccatgactcc aatgtgaag                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagcaccgtc tggccaagac                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaataactg attggtcagg                                                 20

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgttgtatga ccagagatct attttagtgt cct                                  33

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 8
ccatcagatt gaaaagaat tct                                          23

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caggaggtct atatttggtt ccattggc                                    28

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggtggatta aacaaaagca                                             20

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccaatacag gggacatcac atttcttg                                    28

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catgggctga cagtgat                                                17

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtgacagga ttggtcttgt ctttagc                                     27

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ctaaccgagg tcgaaac                                                    17

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatgcagctt ttgccttcaa cagag                                           25

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtccaaccc taattccaa                                                  19

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctccctcta taaaacctgc tatagctcca aa                                   32

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgactgggct cagaaa                                                     16

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cgcgactagg gaactcgctc gcg                                             23

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
```
cgcggattgg cttttttactt tctcaccgcg     30

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ggcggatgct gctcccacta ccgcc     25

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
cgctgaaagc gtttctcgag gtcctg     26

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gcgagtttgc atgttctcct gtctcgc     27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gccgctccat tgaaaccatt acgcggc     27

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gcgctataga gagaacagcg c     21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ggccgcctat tacctctcgg cc     22

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caggaactct agaaa                                                    15

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tcctctcttt tttcttcttc tct                                           23

<210> SEQ ID NO 29
<211> LENGTH: 989
<212> TYPE: DNA
<213> ORGANISM: Influenza virus

<400> SEQUENCE: 29
tagatattga aagatgagcc ttctaaccga ggtcgaaacg tatgttctct ctatcgttcc    60
atcaggcccc ctcaaagccg aaatcgcgca gagacttgaa gatgtctttg ctgggaaaaa   120
cacagatctt gaggctctca tggaatggct aaagacaaga ccaatcctgt cacctctgac   180 taagggatt ttggggtttg tgttcacgct caccgtgccc agtgagcgag gactgcagcg    240
tagacgcttt gtccaaaatg ccctcaatgg gaatggggat ccaaataaca tggacaaagc   300
agttaaactg tatagaaaac ttaagaggga gataacattc catggggcca agaaatagc    360 actcagttat tctgctggtg cacttgccag ttgcatgggc tcatataca ataggatggg    420 ggctgtaacc accgaagtgg catttggcct ggtatgtgca acatgtgaac agattgctga   480
ctcccagcac aggtctcata ggcaaatggt ggcaacaacc aatccattaa taaaacatga   540
gaacaggatg gttttggcca gcactacagc taaagctatg gagcaaatgg ctggatcaag   600
tgagcaggca gcggaggcca tggagattgc tagtcaggcc aggcaaatgg tgcaggcaat   660
gagaaccgtt gggactcatc ctagctccag tactggtcta agagatgatc ttcttgaaaa   720
tttgcagacc tatcagaaac gaatgggggt gcagatgcaa cgattcaagt gacctgcttg   780
ttgttgctgc gagtatcatt gggatcttgc acttgatatt gtggattctt gatcgtcttt   840
ttttcaaatg catctatcga ctcttcaaac acggcctgaa agagggcct tctacggaag    900 gagtacctga gtctatgagg gaagaatatc gaaggaaca gcagaatgct gtggatgctg   960
acggcagtca ttttgtcagc atagagctg                                     989

<210> SEQ ID NO 30
<211> LENGTH: 985
<212> TYPE: DNA
<213> ORGANISM: Influenza virus

<400> SEQUENCE: 30
atgagtcttc taaccgaggt cgaaacgtac gttctctcta tcgtcccgtc aggccccctc    60
aaagccgaga tcgcacagag acttgaaaat gtctttgctg gaaagaatac cgatcttgag   120

```
gctctcatgg aatggctaaa gacaagacca atcctgtcac ctctgactaa ggggattttta    180 ggatttgtgt tcacgctcac cgtgcccagt gagcgaggac tgcagcgtag acgctttgtc    240
caaaatgccc ttaatgggaa tggggatcca ataatatgg acagagcagt taaactgtat     300
cgaaagctta gagggagat aacattccat ggggccaaag aaatagcact cagttattct     360
gctggtgcac ttgccagttg tatgggactc atatacaaca ggatggggc tgtgaccacc     420 gaatcagcat ttggccttat atgcgcaacc tgtgaacaga ttgccgactc ccagcataag    480
tctcataggc aaatggtaac aacaaccaac ccattaataa gacatgagaa cagaatggtt    540
ctggccagca ctacagctaa ggctatggag caaatggctg gatcgagtga acaagcagct    600
gaggccatgg aggttgctag tcaggccagg cagatggtgc aggcaatgag agccattggg    660
actcatccta gctctagcac tggtctgaaa aatgatctcc ttgaaaattt gcaggcctat    720
cagaaacgaa tggggtgca gatgcaacga ttcaagtgat cctcttgttg ttgccgcaag    780
tataattggg attgtgcacc tgatattgtg gattattgat cgccttttt ccaaaagcat    840 ttatcgtatc tttaaacacg gtttaaaaag agggccttct acggaaggag taccagagtc    900
tatgagggaa gaatatcgag aggaacagca gaatgctgtg gatgctgacg atggtcattt    960
tgtcagcata gagctggagt aaaaa                                          985

<210> SEQ ID NO 31
<211> LENGTH: 1039
<212> TYPE: DNA
<213> ORGANISM: Influenza virus

<400> SEQUENCE: 31
agcaaaagca ggtagatgtt gaaagatgag tcttctaacc gaggtcgaaa cgtacgttct     60
ctctatcatc ccgtcaggcc ccctcaaagc cgagatcgcg cagaaacttg aagatgtctt    120
tgcaggaaag aacaccgatc tcgaggctct catggagtgg ctaaagacaa gaccaatcct    180
gtcacctctg actaaaggga ttttgggatt tgtattcacg ctcaccgtgc ccagtgagcg    240
aggactgcag cgtagacgct ttgtccagaa tgccctaaat ggaaatggag atccaaataa    300
tatggataga gcagtcaagc tatataagaa gctgaaaaga gaaataacat tccatggggc    360
taaggaggtc gcactcagct actcaaccgg tgcacttgcc agttgcatgg gtctcatata    420
caacaggatg ggaacggtga ctacggaagt ggcttttggc ctagtgtgtg ccacttgtga    480
gcagattgca gattcacagc atcggtctca cagacagatg gcaactacca ccaacccact    540
aatcagacat gagaacagaa tggtgctggc cagcactaca gctaaggcta tggagcagat    600
ggcaggatca agtgagcagg cagcggaagc catggagatc gctaatcagg ctaggcagat    660
ggtgcaggca atgaggacaa ttgggactca tcctaactct agtgctggtc tgagagataa    720
tcttcttgaa aatttgcagg cctaccagaa acgaatggga gtgcagatgc agcgattcaa    780
gtgatcctat tgttgttgcc gcaaatatca ttgggatctt gcacttgata ttgtggattc    840
ttgatcgtct tttcttcaaa tgcatttatc gtcgccttaa atacggtttg aaaagagggc    900
ctgctacggc agggtaccct gagtctatga gggaagagta ccggcaggaa cagcagagtg    960
ctgtggatgt tgacgatggt catttttgtca acatagaatt ggagtaaaaa actaccttgt   1020
ttctactaat acggaagac                                                 1039

<210> SEQ ID NO 32
<211> LENGTH: 1076
<212> TYPE: DNA
<213> ORGANISM: Influenza virus
```

<400> SEQUENCE: 32

```
atgtcgctgt tggagacac aattgcctac ctgctttcat tgacagaaga tggagaaggc      60
aaagcagaac tagcagaaaa attacactgt tggttcggtg ggaagaatt tgacctagac     120
tctgccctgg aatggataaa aaacaaaaga tgcttaactg atatacaaaa agcactaatt    180
ggtgcctcta tctgcttttt aaaacccaaa gaccaggaaa gaaaagaag attcatcaca     240
gagcctctat caggaatggg aacaacagca acaaaaaaga aaggcctgat tctagctgag    300
agaaaaatga aagatgtgt gagctttcat gaagcatttg aaatagcaga aggccatgaa     360
agctcagcgc tactatactg tctcatggtc atgtacctga tcctggaaa ttattcaatg     420
caagtaaaac taggaacgct ctgtgctttg tgcgagaaac aagcatcaca ttcacacagg    480
gctcatagca gagcagcgag atcttcagtg cctggagtga cgagaaat gcagatggtc      540
tcagctatga acacagcaaa acaatgaat ggaatgggaa aggagaaga cgtccaaaaa      600
ctggcagaag agctgcaaag caacattgga gtactgagat ctcttgggc aagtcaaaag     660
aatggagaag gaattgcaaa ggatgtaatg gaagtgctaa agcagagctc tatgggaaat    720
tcagctcttg tgaagaaata tctataatgc tcgaaccatt tcagattctt tcaatttgtt    780
cttttatctt atcagctctc catttcatgg cttggacaat agggcatttg aatcaaataa    840
aaagaggagt aaacatgaaa atacgaataa aagtccaaaa caaagagaca ataaacagag    900
aggtatcaat tttgagacac agttaccaaa aagaaatcca ggccaaagaa acaatgaagg    960
aggtactctc tgacaacatg gaggtattga gtgaccacat aataattgag gggctttctg   1020
ccgaagagat aataaaaatg ggtgaaacag ttttggagat agaagaattg cattaa        1076
```

<210> SEQ ID NO 33
<211> LENGTH: 1736
<212> TYPE: DNA
<213> ORGANISM: Influenza virus

<400> SEQUENCE: 33

```
tcatctgtca aatggagaaa atagtgcttc tttttgcaat agtcagtctt gttaaaagtg      60
atcagatttg cattggttac catgcaaaca actcgacaga gcaggttgac acaataatgg     120
aaaagaacgt tactgttaca catgcccaag acatactgga aaagacacac aacgggaagc     180
tctgcgatct agatggagtg aagcctctaa ttttgagaga ttgtagtgta gctggatggc     240
tcctcggaaa cccaatgtgt gacgaattca tcaatgtgcc ggaatggtcc tacatagtgg     300
agaaggccaa tccagtcaat gacctctgtt acccagggga tttcaatgac tatgaagaat    360
tgaaacacct attgagcaga ataaaccatt ttgagaaaat tcagatcatc cccaaaagtt    420
cttggtccag tcatgaagcc tcattagggg tgagctcagc atgtccatac agagaaagt     480
cctccttttt cagaaatgtg gtatggctta tcaaaagaa cagtacatac ccaacaataa     540
agaggagcta caataatacc aaccaagaag atcttttggt actgtggggg attcaccatc    600
ctaatgatgc ggcagagcag acaaagctct atcaaaaccc aaccacctat atttccgttg    660
ggacatcaac actaaaccag agattggtac caagaatagc tactagatcc aaagtaaacg    720
ggcaaagtgg aaggatggag ttcttctgga caatttaaa accgaatgat gcaatcaact    780
tcgagagtaa tggaaattc attgctccag aatatgcata caaaattgtc aagaaagggg    840
actcaacaat tatgaaaagt gaattggaat atggtaactg caacaccaag tgtcaaactc    900
caatgggggc gataaactct agtatgccat tccacaatat acaccctctc accatcgggg    960
aatgccccaa atatgtgaaa tcaaacagat tagtccttgc gactgggctc agaaatagcc   1020
```

-continued

| | |
|---|---|
| ctcaaagaga gagaagaaga aaaaagagag gattatttgg agctatagca ggttttatag | 1080 |
| agggaggatg gcagggaatg gtagatggtt ggtatgggta ccaccatagc aatgagcagg | 1140 |
| ggagtgggta cgctgcagac aaagaatcca ctcaaaaggc aatagatgga gtcaccaata | 1200 |
| aggtcaactc gatcattgac aaaatgaaca ctcagtttga ggccgttgga agggaattta | 1260 |
| acaacttaga aaggagaata gagaatttaa acaagaagat ggaagacggg ttcctagatg | 1320 |
| tctggactta taatgctgaa cttctggttc tcatggaaaa tgagagaact ctagactttc | 1380 |
| atgactcaaa tgtcaagaac ctttacgaca aggtccgact acagcttagg gataatgcaa | 1440 |
| aggaactggg taacggttgt tcgagttct atcataaatg tgataatgaa tgtatggaaa | 1500 |
| gtgtaagaaa cggaacgtat gactacccgc agtattcaga agaagcaaga ctaaaaagag | 1560 |
| aggaaataag tggagtaaaa ttggaatcaa taggaattta ccaaatactg tcaatttatt | 1620 |
| ctacagtggc gagttcccta gcactggcaa tcatggtagc tggtctatcc ttatggatgt | 1680 |
| gctccaatgg gtcgttacaa tgcagaattt gcatttaaat ttgtgagttc agattg | 1736 |

<210> SEQ ID NO 34
<211> LENGTH: 1692
<212> TYPE: DNA
<213> ORGANISM: Influenza virus

<400> SEQUENCE: 34

| | |
|---|---|
| atgaaagcaa aactactggt cctgttatgt acatttacag ctacatatgc agacacaata | 60 |
| tgtataggct accatgccaa caactcaacc gacactgttg acacagtact tgagaagaat | 120 |
| gtgacagtga cacactctgt caacctactt gaggacagtc acaacggaaa actatgtcta | 180 |
| ctaaaaggaa tagccccact acaattgggt aattgcagcg ttgccggatg gatcttagga | 240 |
| aacccagaat gcgaattact gatttccaag gaatcatggt cctacattgt agaaacacca | 300 |
| aatcctgaga tggaacatg ttacccaggg tatttcgccg actatgagga actgagggag | 360 |
| caattgagtt cagtatcttc atttgagaga ttcgaaatat tccccaaaga aagctcatgg | 420 |
| cccaaccaca ccgtaaccgg agtatcagca tcatgctccc ataatgggaa agcagttttt | 480 |
| tacagaaatt tgctatggct gacggggaag aatggtttgt acccaaaccct gagcaagtcc | 540 |
| tatgtaaaca caaagagaa agaagtcctt gtactatggg gtgttcatca cccgcctaac | 600 |
| atagggggacc aaagggccct ctatcataca gaaaatgctt atgtctctgt agtgtcttca | 660 |
| cattatagca gaagattcac cccagaaata gccaaaagac ccaaagtaag gatcaggaa | 720 |
| ggaagaatca actactactg gactctgctg gaacctgggg atacaataat atttgaggca | 780 |
| aatggaaatc taatagcgcc atggtatgct tttgcactga gtagaggctt tggatcagga | 840 |
| atcatcacct caaatgcacc aatggatgaa tgtgatgcga agtgtcaaac acctcaggga | 900 |
| gctataaaca gcagtcttcc tttccagaat gtacacccag tcacaatagg agagtgtcca | 960 |
| aagtatgtca ggagtgcaaa attaaggatg gttacggac taaggaacat cccatccatt | 1020 |
| caatccagag gtttgtttgg agccattgcc ggtttcattg aaggggggtg gactggaatg | 1080 |
| gtagatgggt ggtatggtta tcatcatcag aatgagcaag gatctggcta tgctgcagat | 1140 |
| caaaaaagta cacaaaatgc cattaacggg attacaaaca aggtgaattc tgtaattgag | 1200 |
| aaaatgaaca ctcaattcac agctgtgggc aaagaattca acaaattgga agaaggatg | 1260 |
| gaaaacttaa ataaaaagt tgatgatggg tttctagaca ttggacata taatgcagaa | 1320 |
| ttgttggttc tactggaaaa tgaaaggact ttggatttcc atgactccaa tgtgaagaat | 1380 |
| ctgtatgaga agtaaaaag ccaattaaag aataatgcca agaaaatagg aaacggtgt | 1440 |

```
tttgaattct atcacaagtg taacaatgaa tgcatggaga gtgtgaaaaa tggaacttat    1500
gactatccaa atattccga agaatcaaag ttaaacaggg agaaaattga tggagtgaaa    1560
ttggaatcaa tgggagtcta tcagattctg gcgatctact caactgtcgc cagttccctg    1620
gttcttttgg tctccctggg ggcaatcagc ttctggatgt gttccaatgg gtctttgcag    1680
tgcagaatat gc                                                         1692
```

<210> SEQ ID NO 35
<211> LENGTH: 1718
<212> TYPE: DNA
<213> ORGANISM: Influenza virus

<400> SEQUENCE: 35

```
tattaaccat gaagactatc attgctttga gctacattct atgtctggtt ttcgctcaaa      60
aacttcccgg aaatgacaac agcacggcaa cgctgtgcct gggcaccat gcagtaccaa     120 acggaacgat agtgaaaaca atcacgaatg accaaattga agttactaat gctactgagc     180
tggttcagag ttcctcaaca ggtggaatat gcgacagtcc tcatcagatc cttgatggag     240
aaaactgcac actaatagat gctctattgg gagaccctca gtgtgatggc ttccaaaata     300
agaaatggga ccttttgtt gaacgcagca agcctacag caactgttac ccttatgatg     360
tgccggatta tgcctcccttt aggtcactag ttgcctcatc cggcacactg gagtttaaca     420
atgaaagctt caattggact ggagtcactc aaaatggaac aagctctgct tgtaaaagga     480
gatctaataa cagtttcttt agtagattga attggttgac ccacttaaaa ttcaaatacc     540
cagcattgaa cgtgactatg ccaaacaatg aaaaatttga caaattgtac atttggggg     600 ttcaccaccc gggtacggac aatgaccaaa ttagcctata tgctcaagct tcaggaagaa     660
tcacagtctc taccaaaaga agccaacaaa ctgtaatccc gaatatcgga tctagaccca     720
gggtaaggga tatccccagc agaataagca tctattggac aatagtaaaa ccggagaca     780 tacttttgat taacagcaca gggaatctaa ttgctcctcg gggttacttc aaaatacgaa     840
gtgggaaaag ctcaataatg agatcagatg cacccattgg caaatgcaat tctgaatgca     900
tcactccaaa tggaagcatt cccaatgaca aaccatttca aaatgtaaac aggatcacat     960
atggggcctg tcccagatat gttaagcaaa acactctgaa attggcaaca gggatgcgaa    1020
atgtaccaga gaaacaaact agaggcatat ttggcgcaat gcgggtttc atagaaaatg    1080 gttgggaggg aatggtggat ggttggtacg gtttcaggca tcaaaattct gagggaatag    1140
gacaagcagc agatctcaaa agcactcaag cagcaatcaa ccaaatcaat gggaagctga    1200
ataggttgat cgggaaaacc aacgagaaat ccatcagat tgaaaagaa ttctcagaag    1260 tagaagggag aattcaggac ctcgagaaat atgttgagga cactaaaata gatctctggt    1320
catacaacgc ggagcttctt gttgccctgg agaaccaaca tacaattgat ctaactgact    1380
cagaaatgaa caaactgttt gaaagaacaa agaagcaact gagggaaaat gctgaggata    1440
tgggcaatgg ttgtttcaaa atataccaca atgtgacaa tgcctgcata gggtcaatca    1500
gaaatggaac ttatgaccat gatgtataca gagatgaagc attaaacaac cggttccaga    1560
tcaaaggtgt tgagctgaag tcaggataca agattggat cctatggatt cctttgcca    1620 tatcatgttt tttgctttgt gttgttttgt tggggttcat catgtgggcc tgccaaaaag    1680
gcaacattag gtgcaacatt tgcatttgag tgcattaa                            1718
```

<210> SEQ ID NO 36
<211> LENGTH: 1038
<212> TYPE: DNA

<213> ORGANISM: Influenza virus

<400> SEQUENCE: 36

| | | | | | |
|---|---|---|---|---|---|
| gatcgaatct | gcactgggat | aacatcttca | aactcacctc | atgtggtcaa | aacagctact | 60 |
| caaggggagg | tcaatgtgac | tggtgtgata | ccactgacaa | caacaccaac | aaaatcttat | 120 |
| tttgcaaatc | tcaaggaac | aaggaccaga | gggaaactat | gcccagactg | tctcaactgt | 180 |
| acagatctgg | atgtggcctt | gggcaggcca | atgtgtgtgg | ggaccacacc | ttctgcgaaa | 240 |
| gcttcaatac | tccacgacct | gttacatccg | ggtgctttcc | tataatgcac | gacagaacaa | 300 |
| aaatcgaagt | caaggcaact | agccaatctt | ctcagaggat | atgaaaatat | caggttatca | 360 |
| acccaaaacg | ttatcgatgc | agaaaaggca | ccaggaggac | cctacagact | tggaacctca | 420 |
| ggatcttgcc | ctaacgctac | cagtaaaagc | ggattttttcg | caacaatggc | ttgggctgtc | 480 |
| ccaaaggaca | caacaaaaa | tgcaacgaac | ccactaacag | tagaagtacc | atacatttgt | 540 |
| acagaagggg | aagaccaaat | tactgttttgg | gggttccatt | cagataacaa | acccaaatg | 600 |
| aagaacctct | atggagactc | aaatcctcaa | aagttcacct | catctgctaa | tggagtaacc | 660 |
| acacattatg | tttctcagat | tggcggcttc | ccagatcaaa | cagaagacgg | aggactacca | 720 |
| caaagcggca | gaattgtcgt | tgattacatg | atgcaaaaac | ctgggaaaac | aggaacaatt | 780 |
| gtctatcaaa | gaggtgtttt | gttgcctcaa | aaggtgtggt | gcgcgagtgg | caggagcaaa | 840 |
| gtaataaaag | ggtccttgcc | tttaattggt | gaagcagatt | gccttcatga | aaaatacggt | 900 |
| ggattaaaca | aaagcaagcc | ttactacaca | ggagaacatg | caaaagccat | aggaaattgc | 960 |
| ccaatatggg | tgaaaacacc | tttgaagctt | gccaatggaa | ccaaatatag | acctcctgca | 1020 |
| aaactattaa | aggaaagg | | | | | 1038 |

<210> SEQ ID NO 37
<211> LENGTH: 1409
<212> TYPE: DNA
<213> ORGANISM: Influenza virus

<400> SEQUENCE: 37

| | | | | | |
|---|---|---|---|---|---|
| atgaatccaa | atcaaaaaat | aataaccatt | ggatcaatca | gtatagcaat | cggaataatt | 60 |
| agtctaatgt | tgcaaatagg | aaatattatt | tcaatatggg | ctagtcactc | aatccaaact | 120 |
| ggaagtcaaa | accacactgg | agtatgcaac | caaagaatca | tcacatatga | aaacagcacc | 180 |
| tgggtgaatc | acacatatgt | taatattaac | aacactaatg | ttgttgctgg | aaaggacaaa | 240 |
| acttcagtga | cattggccgg | caattcatct | ctttgttcta | tcagtggatg | ggctatatac | 300 |
| acaaaagaca | acagcataag | aattggctcc | aaggagatg | ttttgtcat | aagagaacct | 360 |
| ttcatatcat | gttctcactt | ggaatgcaga | accttttttc | tgacccaagg | tgctctatta | 420 |
| aatgacaaac | attcaaatgg | gaccgttaag | gacagaagtc | cttatagggc | cttaatgagc | 480 |
| tgtcctctag | tgtgaagctcc | gtccccatac | aattcaaagt | ttgaatcagt | tgcatggtca | 540 |
| gcaagcgcat | gccatgatgg | catgggctgg | ttaacaatcg | gaatttctgg | tccagacaat | 600 |
| ggagctgtgg | ctgtactaaa | atacaacggc | ataataactg | aaaccataaa | aagttggaaa | 660 |
| aagcgaatat | taagaacaca | agagtctgaa | tgtgtctgtg | tgaacgggtc | atgtttcacc | 720 |
| ataatgaccg | atggcccgag | taatgggcc | gcctcgtaca | aaatcttcaa | gatcgaaaag | 780 |
| gggaaggtta | ctaaatcaat | agagttgaat | gcacccaatt | ttcattatga | ggaatgttcc | 840 |
| tgttaccag | acactggcac | agtgatgtgt | gtatgcaggg | acaactggca | tggttcaaat | 900 |
| cgaccttggg | tgtctttaa | tcaaaacctg | gattatcaaa | taggatacat | ctgcagtggg | 960 |

```
gtgttcggtg acaatccgcg tcccaaagat ggagagggca gctgtaatcc agtgactgtt      1020
gatggagcag acgagtaaa gggttttca tacaaatatg gtaatggtgt ttggatagga        1080
aggactaaaa gtaacagact tagaaagggg tttgagatga tttgggatcc taatggatgg     1140
acagataccg acagtgattt ctcagtgaaa caggatgttg tggcaataac tgattggtca     1200
gggtacagcg gaagtttcgt tcaacatcct gagttaacag gattggactg tataagacct    1260
tgcttctggg ttgagttagt cagaggactg cctagaaaa atacaacaat ctggactagt      1320
gggagcagca tttcttttg tggcgtaaat agtgatactg caaactggtc ttggccagac      1380
ggtgctgagt tgccattcac cattgacaa                                       1409

<210> SEQ ID NO 38
<211> LENGTH: 1392
<212> TYPE: DNA
<213> ORGANISM: Influenza virus

<400> SEQUENCE: 38
ttattggtct cagggagcaa aagcaggagt tcaaaatgaa tccaaataag aagataataa      60
ccatcggatc aatctgtatg gtaactggaa tggttagctt aatgttacaa attgggaact     120
tgatctcaat atgggtcagt cattcaattc acacagggaa tcaacacaaa gctgaaccaa     180
tcagcaatac taatttttctt actgagaaag ctgtggcttc agtaaaatta gcgggcaatt    240
catctctttg ccccattaat ggatgggctg tatacagtaa ggacaacagt ataaggatcg      300
gttccaaggg ggatgtgttt gttataagag agccattcat ctcatgctcc cacttggaat    360
gcagaacttt cttttttgact cagggagcct tgctgaatga caagcactcc aatgggactg   420
tcaaagacag aagccctcac agaacattaa tgagttgtcc tgtgggtgag gctccctccc    480
catataactc aaggtttgag tctgttgctt ggtcagcaag tgcttgccat gatggcacca    540
gttggttgac aattggaatt tctggcccag acaatgggc tgtggctgta ttgaaataca    600
atggcataat aacagacact atcaagagtt ggaggaataa catactgaga actcaagagt    660
ctgaatgtgc atgtgtaaat ggctcttgct ttactgtaat gactgacgga ccaagtaatg     720
gtcaggcatc acataagatc ttcaaaatgg aaaaaggaa agtggttaaa tcagtcgaat      780
tggatgctcc caattatcac tatgaggaat gctcctgtta tcctgatgcc ggcgaaatca     840
catgtgtgtg cagggataat tggcatggct caaatcggcc atgggtatct ttcaatcaaa    900
atttggagta tcaaatagga tatatatgca gtggagtttt tggagacaat ccacgcccca     960
atgatggaac aggtagttgt ggtccggtgt cctctaacgg ggcatatggg gtaaaagggt   1020
tttcatttaa atacggcaat ggtgtctgga tcgggagaac aaaaagcact aattccagga    1080
gcggctttga aatgatttgg gatccaaatg ggtggactga aacggacagt agcttttcag   1140
tgaaacaaga tatcgtagca ataactgatt ggtcaggata tagcgggagt tttgtccagc    1200
atccagaact gacaggacta gattgcataa gaccttgttt ctgggttgag ttgatcagag   1260 gcggcccaa agagagcaca atttggacta gtgggagcag catatctttt tgtggtgtaa    1320
atagtgacac tgtgggttgg tcttggccag acggtgctga attgccattc accattgaca   1380
agtagttgtt ca                                                        1392

<210> SEQ ID NO 39
<211> LENGTH: 1410
<212> TYPE: DNA
<213> ORGANISM: Influenza virus

<400> SEQUENCE: 39
```

-continued

| | |
|---|---|
| atgaatccaa atcaaaagat aataacgatt ggctctgttt ctctcaccat ttccacaata | 60 |
| tgcttcttca tgcaaattgc catcttgata actactgtaa cattgcattt caagcaatat | 120 |
| gaattcaact ccccccccaaa caaccaagtg atgctgtgtg aaccaacaat aatagaaaga | 180 |
| aacataacag atagtgtata tctgaccaac accaccatag agaaggaaat atgccccaaa | 240 |
| ctagcagaat acagaaattg gtcaaagccg caatgtaaca ttacaggatt tgcacctttt | 300 |
| tctaaggaca attcgattag gctttccgct ggtgggggaca tctgggtgac aagagaacct | 360 |
| tatgtgtcat gcgatcctga caagtgttat caatttgccc ttgggcaggg aacaacacta | 420 |
| aacaacgtgc attcaaatga cacagtacat gataggaccc cttatcggac cctattgatg | 480 |
| aatgagttag gtgttccatt tcatctgggg accaagcaag tgtgcatagc atggtccagc | 540 |
| tcaagttgtc acgatggaaa agcatggctg catgtttgtg taacggggga tgataaaaat | 600 |
| gcaactgcta gcttcattta caatgggagg cttgtagata gtattgtttc atggtccaaa | 660 |
| gaaatcctca ggacccagga gtcagaatgc gtttgtatca tggaacttg tacagtagta | 720 |
| atgactgatg ggagtgcttc aggaaaagct gatactaaaa tactattcat tgaggagggg | 780 |
| aaaatcgttc atactagcac attgtcagga agtgctcagc atgtcgagga gtgctcctgc | 840 |
| tatcctcgat atcttggtgt cagatgtgtc tgcagagaca actggaaagg ctccaatagg | 900 |
| cccatagtag atataaacat aaaggattat agcattgttt ccagttatgt gtgctcagga | 960 |
| cttgttggag acacacccag aaaaaacgac agctccagca gtagccattg cttggatcct | 1020 |
| aacaatgaag aaggtggtca tggagtgaaa ggctgggcct tgatgatgg aaatgacgtg | 1080 |
| tggatgggaa gaacgatcag cgagaagtta cgctcaggat atgaaacctt caaagtcatt | 1140 |
| gaaggctggt ccaaccctaa ttccaaattg cagataaata gcaagtcat agttgacaga | 1200 |
| ggtaataggt ccggttattc tggtattttc tctgttgaag gcaaaagctg catcaatcgg | 1260 |
| tgcttttatg tggagttgat aaggggaaga aaagaggaaa ctgaagtctt gtggacctca | 1320 |
| aacagtattg ttgtgttttg tggcacctca ggtacatatg aacaggctc atggcctgat | 1380 |
| ggggcggaca tcaatctcat gcctatataa | 1410 |

<210> SEQ ID NO 40
<211> LENGTH: 1463
<212> TYPE: DNA
<213> ORGANISM: Influenza virus

<400> SEQUENCE: 40

| | |
|---|---|
| ccaaaatgaa caatgctacc ttcaactata caaacgttaa ccctatttct cacatcaggg | 60 |
| ggagtattat tatcactata tgtgtcagct tcattgtcat acttactata ttcggatata | 120 |
| ttgctaaaat tcccatcaac agaaattact gcaccaacaa tgccattgga ttgtgcaaac | 180 |
| gcatcaaatg ttcaggctgt gaaccgttct gcaacaaaag gggtgacact tcttctccca | 240 |
| gaaccggagt ggacataccc gcgtttatct tgcccggct caacctttca gaaagcactc | 300 |
| ctaattagcc ctcatagatt cggagaaacc aaaggaaact cagctcccctt gataataagg | 360 |
| gaacctttta ttgcttgtgg accaaggaa tgcaaacact ttgctctaac ccactatgca | 420 |
| gcccaaccag ggggatacta caatggaaca agaggagaca gaaacaagct gaggcatcta | 480 |
| atttcagtca aattgggcaa atcccaaca gtagaaaact ccattttcca catggcagca | 540 |
| tggagcgggt ccgcatgcca tgatggtaag gaatggacat atatcggagt tgatggccct | 600 |
| gacaataatg cattgctcaa aataaatat ggagaagcat atactgacac ataccattcc | 660 |
| tatgcaaaca acatcctaag aacacaagaa agtgcctgca attgcatcgg gggaaattgt | 720 |

```
tatcttatga taactgatgg ctcagcttca ggtgttagtg aatgcagatt tcttaagatt    780
cgagagggcc gaataataaa agaaatattt ccaacaggaa gaataaaaca tactgaagaa    840
tgcacatgcg gatttgctag caataaaacc atagaatgtg cctgtagaga taacagttac    900
acagcaaaaa gacccttttgt caaattaaac gtggagactg atacagcaga aataagattg   960
atgtgcacag agacttattt ggacaccccc agaccagatg atggaagcat aacagggcct   1020
tgtgaatcta atggggacaa agggagtgga ggcatcaagg gaggatttgt ccatcaaaga   1080
atggcatcca agattggaag gtggtactct cgaacgatgt ctaaaactaa aaggatgggg   1140
atggggctgt atgtcaagta tgatggagac ccatgggctg acagtgatgc ccttgctttt   1200
agtggagtaa tggtttcaat ggaagaacct ggttggtact cctttggctt cgaaataaaa   1260
gacaagaaat gtgatgtccc ctgtattggg atagagatgg tacatgatgg tggaaaagag   1320
acttggcact cagcagctac agccatttac tgtttaatgg gctcaggaca gctgctgtgg   1380
gacactgtca caggtgttaa tatggctctg taatggagga atggttgagt ctgttctaaa   1440 cccctttgttc ctattttgtt tga                                          1463
```

<210> SEQ ID NO 41
<211> LENGTH: 101
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gtggagtaaa attggaatca ataggaattt accaaatact gtcaatttat tctacagtgg    60
cgagttccct agcactggca atcatggtag ctggtctatc c                       101
```

<210> SEQ ID NO 42
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gtggagtaaa attggaatca ataggaattt accaaatact gtcaatttat tctacagtgc    60
actggcaatc atggtagctg gtctatcc                                      88
```

<210> SEQ ID NO 43
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
ccatgactcc aatgtgaaga atctgtatga gaaagtaaaa agccaattaa agaataatgc    60
caaagaaata ggaaacgggt g                                             81
```

<210> SEQ ID NO 44
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide -continued

<210> SEQ ID NO 44
<400> SEQUENCE: 44
ccatgactcc aatgtgaaga atctgtataa agaataatgc caaagaaata ggaaacgggt    60
g                                                                  61

<210> SEQ ID NO 45
<211> LENGTH: 202
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcaataactg attggtcagg atatagcggg agttttgtcc agcatccaga actgacagga    60
ctagattgca taagaccttg tttctgggtt gagttgatca gagggcggcc caaagagagc   120
acaatttgga ctagtgggag cagcatatct ttttgtggtg taaatagtga cactgtgggt   180
tggtcttggc cagacggtgc tg                                           202

<210> SEQ ID NO 46
<211> LENGTH: 187
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcaataactg attggtcagg atatagcggg agttttgtcc agcatccaga actgacagga    60
ctagattgca taagaccttg tttctgggtt gagttgatca gagggcggcc caaagagagc   120
acaatttgga catcttttg tggtgtaaat agtgacactg tgggttggtc ttggccagac   180
ggtgctg                                                            187

<210> SEQ ID NO 47
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccatcagatt gaaaaagaat tctcagaagt agaagggaga attcaggacc tcgagaaata    60
tgttgaggac actaaaatag atctctggtc atacaacg                           98

<210> SEQ ID NO 48
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccatcagatt gaaaaagaat tctcagaagt agaagggaga atttatgttg aggacactaa    60
aatagatctc tggtcataca acg                                           83

<210> SEQ ID NO 49
<211> LENGTH: 122
<212> TYPE: DNA
<213> ORGANISM: Artificial Sequence
<220> FEATURE:

-continued

<223> OTHER INFORMATION: Description of Artificial Sequence: Synthetic
     oligonucleotide

<400> SEQUENCE: 49
cggtggatta acaaaaagca agccttacta cacaggggaa catgcaaagg ccataggaaa    60
ttgcccaata tgggtgaaaa caccccttgaa gctggccaat ggaaccaaat atagacctcc   120
tg                                                                  122

<210> SEQ ID NO 50
<211> LENGTH: 105
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 50
cggtggatta acaaaaagca agccttacta cggccatagg aaattgccca atatgggtga    60 aaacacccctt gaagctggcc aatggaacca aatatagacc tcctg                  105

<210> SEQ ID NO 51
<211> LENGTH: 119
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 51
catgggctga cagtgatgcc cttgctttta gtggagtaat ggtttcaatg gaagaacctg    60
gttggtactc ctttggcttc gaaataaaag acaagaaatg tgatgtcccc tgtattggg    119

<210> SEQ ID NO 52
<211> LENGTH: 102
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 52
catgggctga cagtgatgcc cttgctttta gtggaagaac ctggttggta ctcctttggc    60
ttcgaaataa aagacaagaa atgtgatgtc ccctgtattg gg                      102

<210> SEQ ID NO 53
<211> LENGTH: 152
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 53
ctaaccgagg tcgaaacgta cgttctctct atcatcccgt caggcccccct caaagccgag   60 atcgcgcaga aacttgaaga tgtctttgca ggaaagaaca ccgatctcga ggctctcatg   120
gagtggctaa agacaagacc aatcctgtca cc                                 152

<210> SEQ ID NO 54
<211> LENGTH: 141
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 54
ctaaccgagg tcgaaacgta ccatcccgtc aggccccctc aaagccgaga tcgcgcagaa    60
acttgaagat gtctttgcag gaaagaacac cgatctcgag gctctcatgg agtggctaaa   120
gacaagacca atcctgtcac c                                            141

<210> SEQ ID NO 55
<211> LENGTH: 107
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtccaaccc taattccaaa ttgcagataa ataggcaagt catagttgac agaggtaata    60
ggtccggtta ttctggtatt ttctctgttg aaggcaaaag ctgcatc                 107

<210> SEQ ID NO 56
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggtccaaccc taattccaaa ttgcagataa ataggcaagt catagttta ttctggtatt     60 ttctctgttg aaggcaaaag ctgcatc                                       87

<210> SEQ ID NO 57
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccatcagatt gaaaagaat tctcagaagt agaagggaga attcaggaac tctagaaata    60
tgttgaggac actaaaatag atctctggtc atacaacg                          98

<210> SEQ ID NO 58
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cgactgggct cagaaatagc cctcaaagag agagaagaag aaaaaagaga ggattatttg    60
gagctatagc aggtttata gagggagg                                      88

<210> SEQ ID NO 59
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
cgactgggct cagaaatagc cctcaaagag ttatttggag ctatagcagg ttttatagag      60
ggagg                                                                 65
```

The invention claimed is:

1. A kit for performing an assay comprising more than one primer pair, more than one detection probe, and a low copy number synthetic amplicon corresponding to each of the primer pairs, wherein the primer pairs are selected from the group consisting of:
   a) CAGCACCGTCTGGCCAAGAC (SEQ ID NO: 5), and GCAATAACTGATTGGTCAGG (SEQ ID NO: 6);
   b) CGTTGTATGACCAGAGATCTATTTTAGTGTCCT (SEQ ID NO: 7), and CCATCAGATTGAAAAAGAATTCT (SEQ ID NO: 8);
   c) CAGGAGGTCTATATTTGGTTCCATTGGC (SEQ ID NO: 9), and CGGTGGATTAAACAAAAGCA (SEQ ID NO: 10);
   d) CCCAATACAGGGGACATCACATTTCTTG (SEQ ID NO: 11), and CATGGGCTGACAGTGAT (SEQ ID NO: 12);
   e) GGTGACAGGATTGGTCTTGTCTTTAGC (SEQ ID NO: 13), and CTAACCGAGGTCGAAAC (SEQ ID NO: 14)
   f) GATGCAGCTTTTGCCTTCAACAGAG (SEQ ID NO: 15), and GGTCCAACCCTAATTCCAA (SEQ ID NO: 16); and
   g) CCTCCCTCTATAAAACCTGCTATAGCTCCAAA (SEQ ID NO: 17), and CGACTGGGCTCAGAAA (SEQ ID NO: 18);
wherein the detection probe is a molecular beacon probe selected from the group consisting of:
   a) Texas Red-CGCGACTAGGGAACTCGCTCGCG (SEQ ID NO: 19)-Dabsyl,
   b) CY3-CGCGGATTGGCTTTTTACTTTCTCACCGCG (SEQ ID NO: 20)-Dabsyl,
   c) FAM- GGCGGATGCTGCTCCCACTACCGCC (SEQ ID NO: 21)-Dabsyl,
   d) CY5-CGCTGAAAGCGTTTCTCGAGGTCCTG (SEQ ID NO: 22)-BHQ1,
   e) Texas Red-GCGAGTTTGCATGTTCTCCTGTCTCGC (SEQ ID NO: 23)-Dabsyl,
   f) CY5-GCGAGTTTGCATGTTCTCCTGTCTCGC (SEQ ID NO: 23)-Dabsyl,
   g) CY3-GCGCTATAGAGAGAACAGCGC (SEQ ID NO: 25)-Dabsyl, Tm=33.8
   h) FAM-GGCCGCCTATTACCTCTCGGCC (SEQ ID NO: 26)-Dabsyl, and
   i) CY5-CGCTGAAAGCGTTTCTCGAGGTCCTG (SEQ ID NO: 22)-BHQ1.

2. The kit according to claim 1
wherein the primer pairs additionally include at least one pair selected from the group consisting of:
   h) GGATAGACCAGCTACCATGATTGCC (SEQ ID NO: 1), and GTGGAGTAAAATTGGAATCAATAGG (SEQ ID NO: 2); and
   i) CACCCGTTTCCTATTTCTTTGGCATTATTC (SEQ ID NO: 3), and CCATGACTCCAATGTGAAG (SEQ ID NO: 4);
wherein the detection probe additionally includes at least one molecular beacon probe selected from the group consisting of:
   j) Texas Red-CGCGACTAGGGAACTCGCTCGCG (SEQ ID NO: 19)-Dabsyl, and
   k) CY3-CGCGGATTGGCTTTTTACTTTCTCACCGCG (SEQ ID NO: 20)-Dabsyl.

3. The kit of claim 1, wherein the low copy number synthetic amplicon comprises approximately twenty copies of the synthetic amplicons per primer pair.

4. The kit of claim 2, comprising all of primer pairs a)-i).

5. The kit of claim 1, further comprising reagents for an amplification reaction.

* * * * *